United States Patent
Laursen et al.

(10) Patent No.: US 9,625,419 B2
(45) Date of Patent: Apr. 18, 2017

(54) CONDUIT SENSOR DEVICE WITH MAGNETIC SHUNT AND PROCESS FOR MODIFYING A MAGNETIC FIELD

(75) Inventors: Paul Laursen, Toronto (CA); Corry Comello, Scarborough (CA); Roderick Lee, Markham (CA)

(73) Assignee: INVODANE ENGINEERING LTD, Toronto (CA)

( * ) Notice: Subject to any disclaimer, the term of this patent is extended or adjusted under 35 U.S.C. 154(b) by 834 days.

(21) Appl. No.: 13/561,924

(22) Filed: Jul. 30, 2012

(65) Prior Publication Data

US 2012/0293289 A1 Nov. 22, 2012

Related U.S. Application Data

(63) Continuation of application No. 12/836,230, filed on Jul. 14, 2010, now Pat. No. 8,232,796.

(51) Int. Cl.
| | | |
|---|---|---|
| *G01N 27/82* | (2006.01) | |
| *G01N 27/72* | (2006.01) | |
| *G01N 27/90* | (2006.01) | |
| *G01R 33/12* | (2006.01) | |

(52) U.S. Cl.
CPC ..... *G01N 27/82* (2013.01); *G01N 2291/2636* (2013.01)

(58) Field of Classification Search
CPC ..................................................... G01N 27/90
USPC ........................................................ 324/220
See application file for complete search history.

(56) References Cited

U.S. PATENT DOCUMENTS

| | | |
|---|---|---|
| 2,698,920 A | 1/1955 | Gieske |
| 4,447,777 A | 5/1984 | Sharp et al. |
| 4,506,219 A | 3/1985 | Lee |
| 5,115,196 A | 5/1992 | Low et al. |
| 5,426,367 A | 6/1995 | Martin et al. |
| 5,565,633 A | 10/1996 | Wernicke |

(Continued)

FOREIGN PATENT DOCUMENTS

KP 20030014502 2/2003

OTHER PUBLICATIONS

European Patent Office, Extended European Search Report, Apr. 14, 2014, European Application No. 11173054.5-1559/2407778, Applicant: Invodane Engineering LTD., pp. 1-9.

(Continued)

*Primary Examiner* — Bot Ledynh

(74) *Attorney, Agent, or Firm* — Woodling, Krost and Rust

(57) ABSTRACT

A conduit sensor device includes first and second pairs of permanent magnets. First and second rotor shunts include first and second rotatable magnets and interposed between the first and second pairs of permanent magnets, respectively. A shunt shaft includes a first helical worm gear and a second helical worm gear mounted thereon. The first rotor shunt includes a first rotatable magnet and a first rotor gear locked together. The first helical worm gear meshing with the first rotor gear driving the first rotor gear and the first rotatable magnet. The second rotor shunt includes a second rotatable magnet and a second rotor gear locked together. The second helical worm gear meshes with the second rotor gear driving the second rotor gear and the second rotatable magnet. The surface areas of the first and second pairs of permanent magnets equals the surface area of the first and second rotatable magnets.

5 Claims, 28 Drawing Sheets

(56) References Cited

U.S. PATENT DOCUMENTS

| | | | |
|---|---|---|---|
| 5,747,998 | A | 5/1998 | Fowler et al. |
| 6,009,756 | A | 1/2000 | Willems et al. |
| 6,085,599 | A * | 7/2000 | Feller .......................... 73/861.13 |
| 6,100,684 | A | 8/2000 | Ramaut |
| 6,762,602 | B1 | 7/2004 | Laursen et al. |
| 2001/0017541 | A1 | 8/2001 | Kwun et al. |
| 2008/0092672 | A1 | 4/2008 | Gibson et al. |

OTHER PUBLICATIONS

European Patent Office, Partial Extended Search Report, Jan. 27, 2014, Application No. 11173054.5-1559/2407778, Applicant: Invodane Engineering Ltd., p. 1-5, Netherlands.

"Tigre: A Robotic Platform and MFL Sensor for the Inspection of Unpiggable Pipelines", Technology Brief, 2008, Northeast Gas Association, http://www.nysearch.org/publications/2008/20-Tigre-052908.pdf.

* cited by examiner

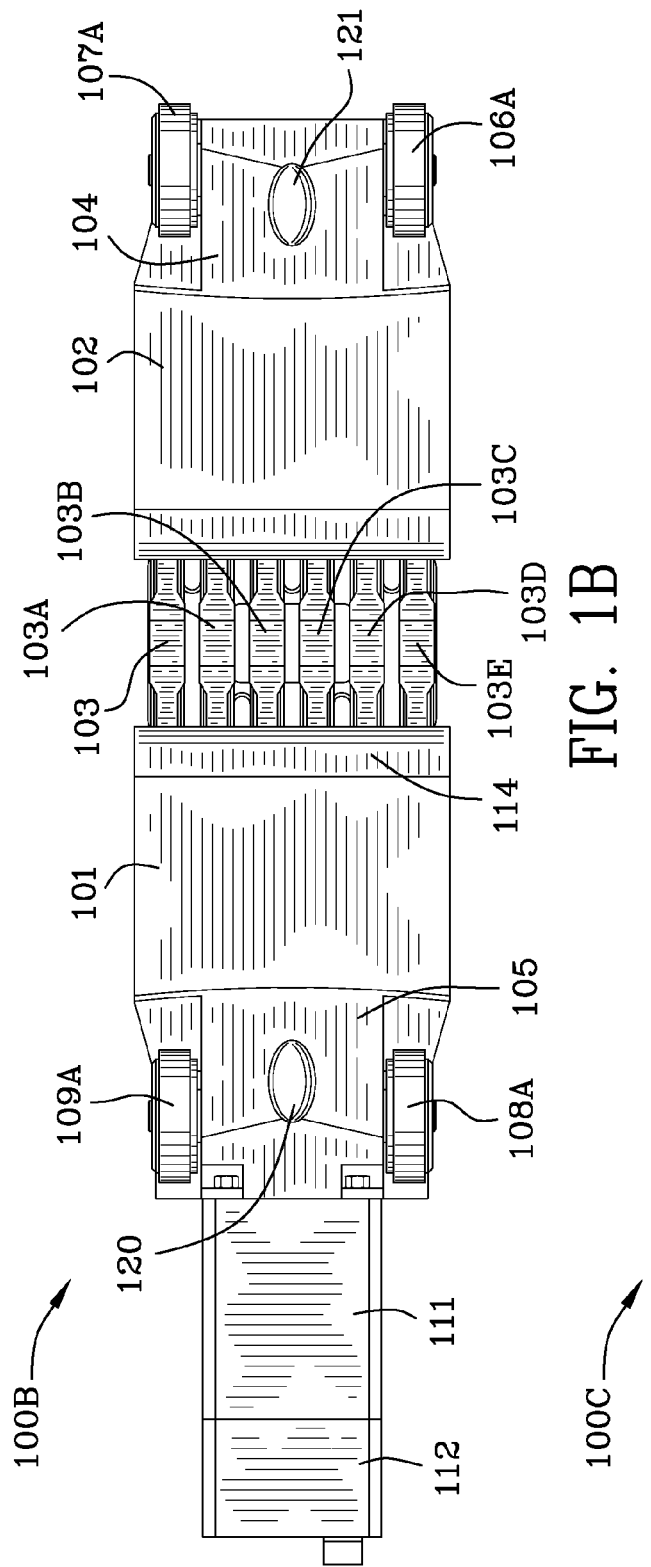
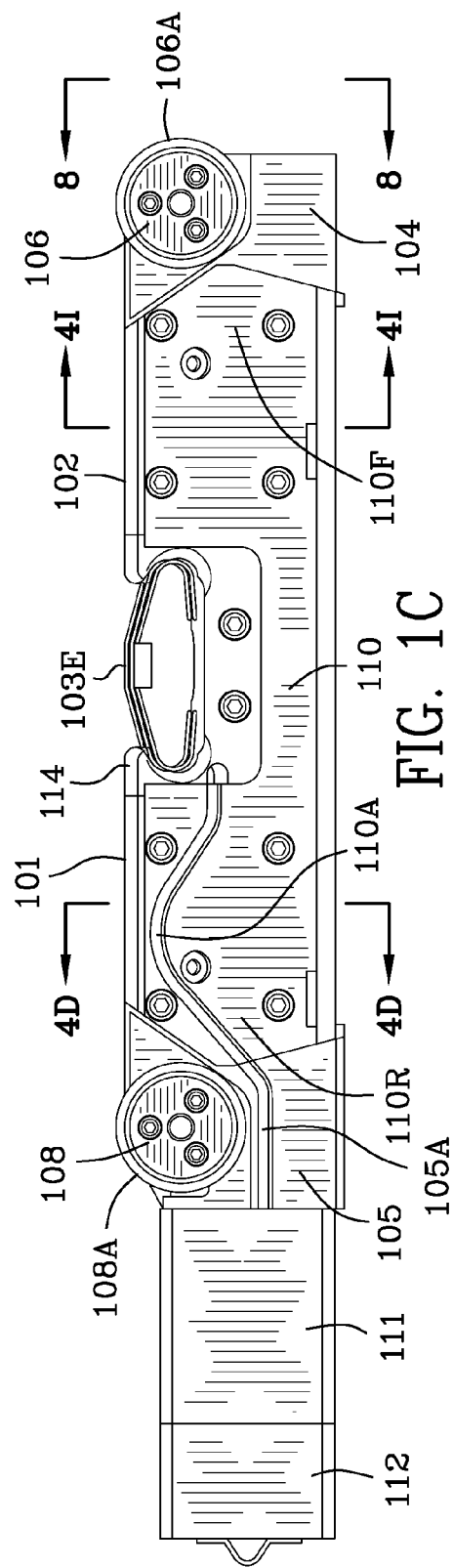

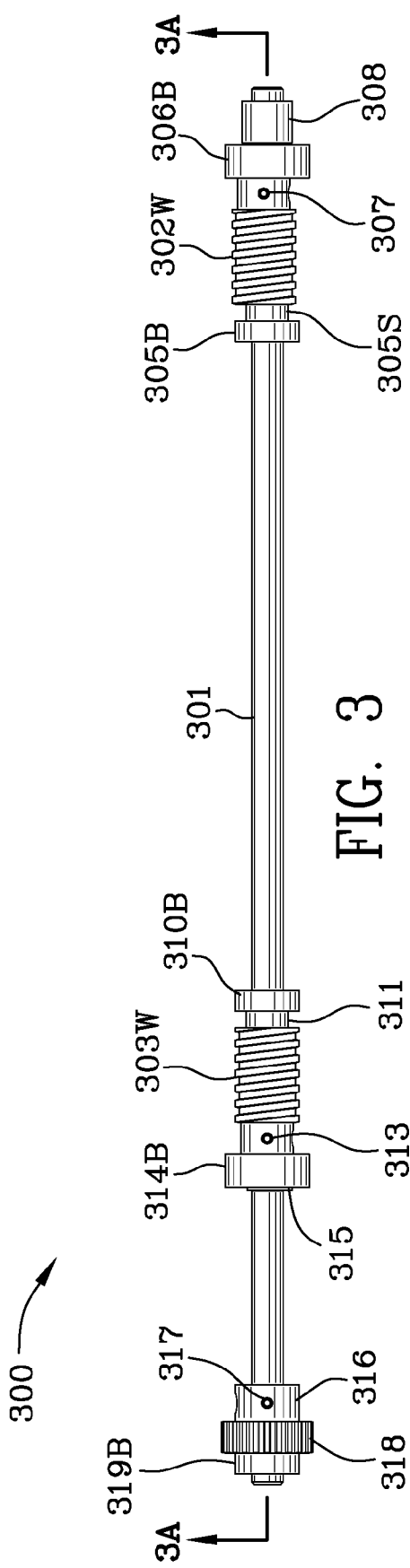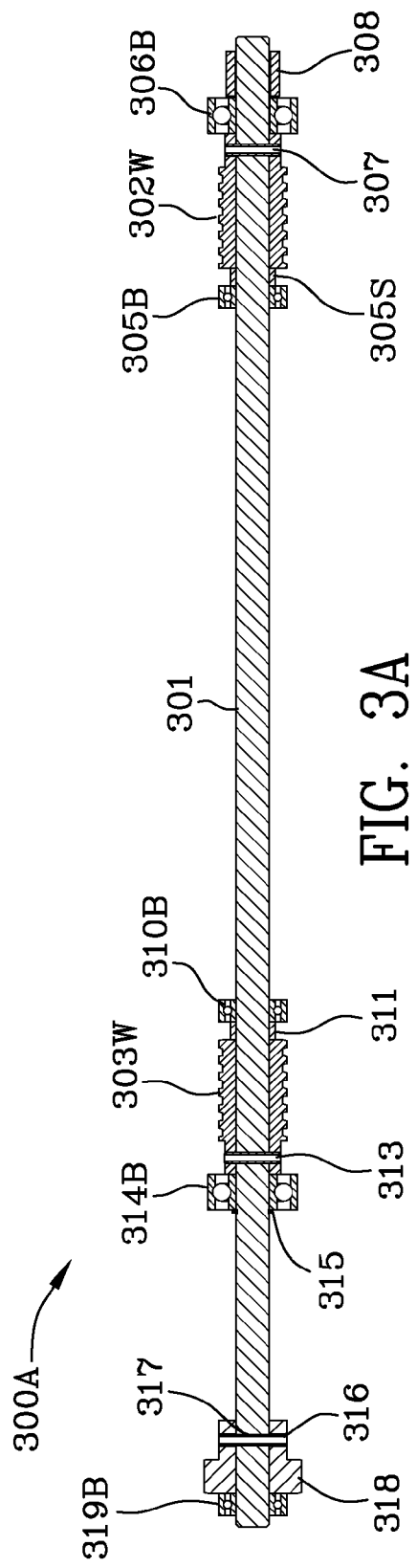

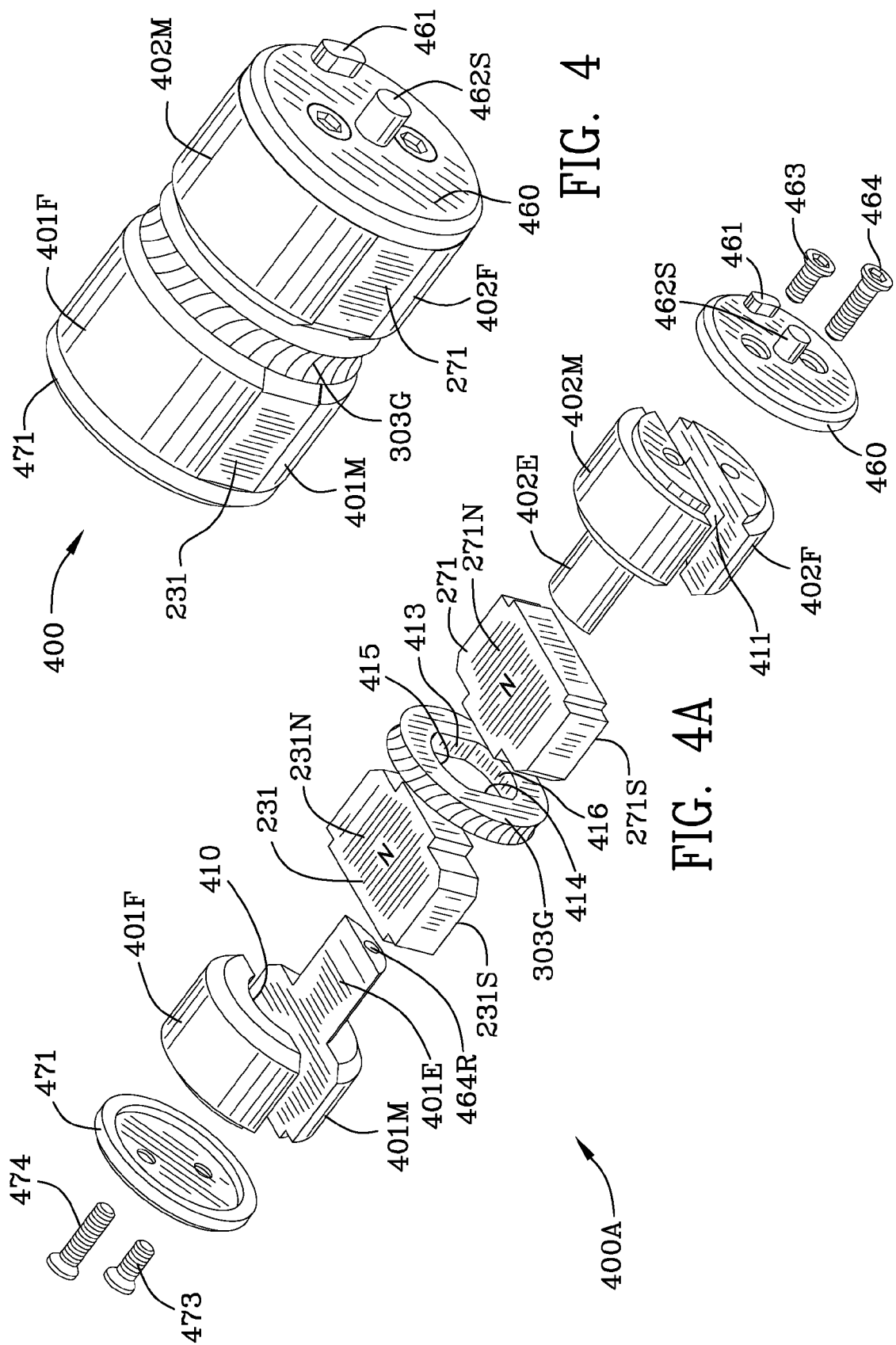

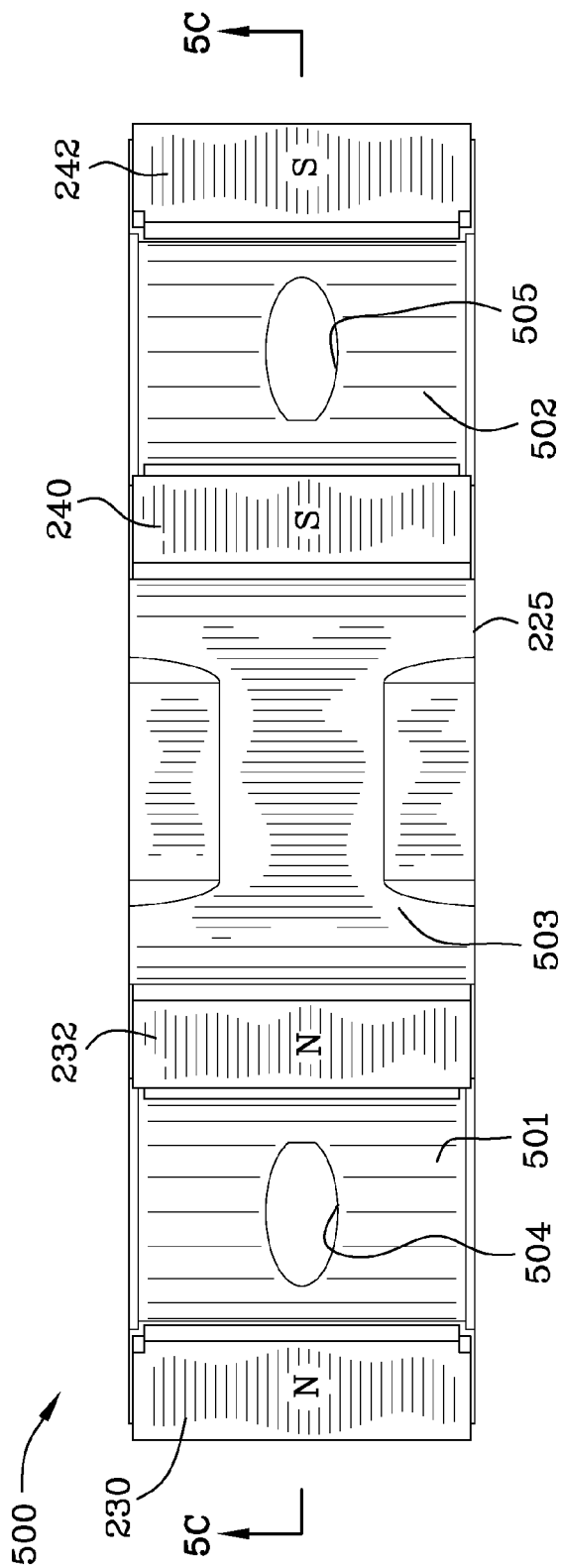
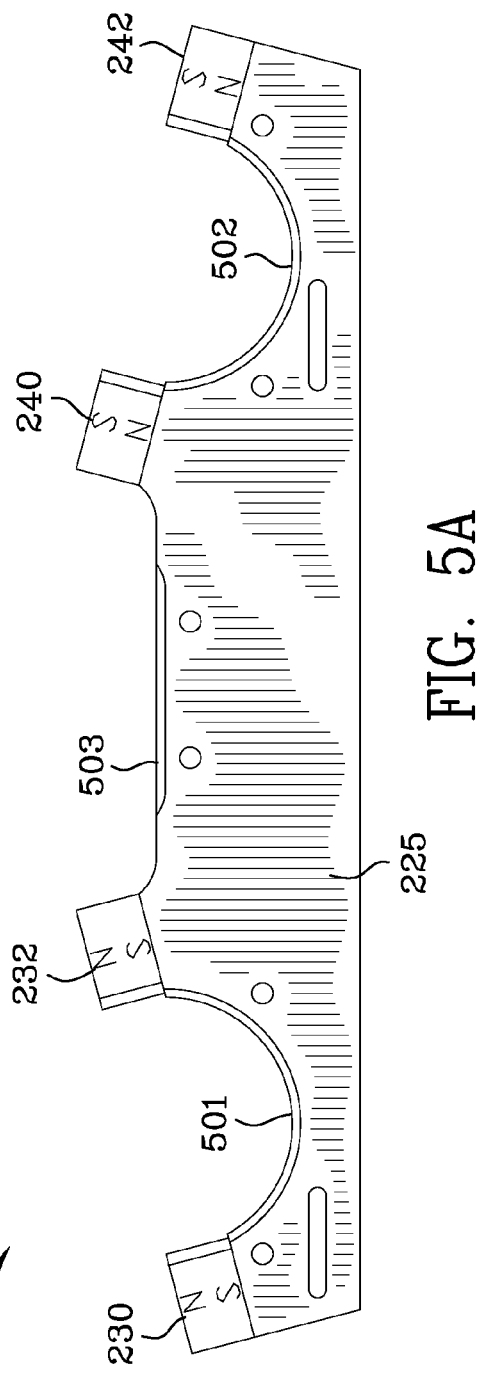
FIG. 5
FIG. 5A

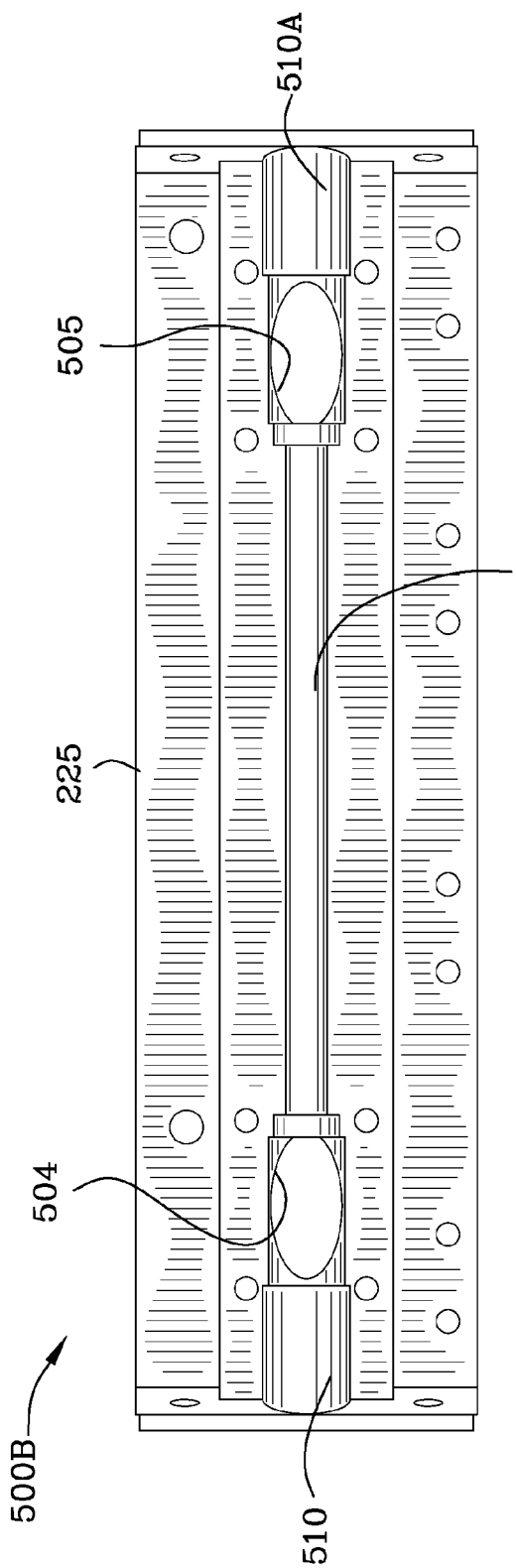
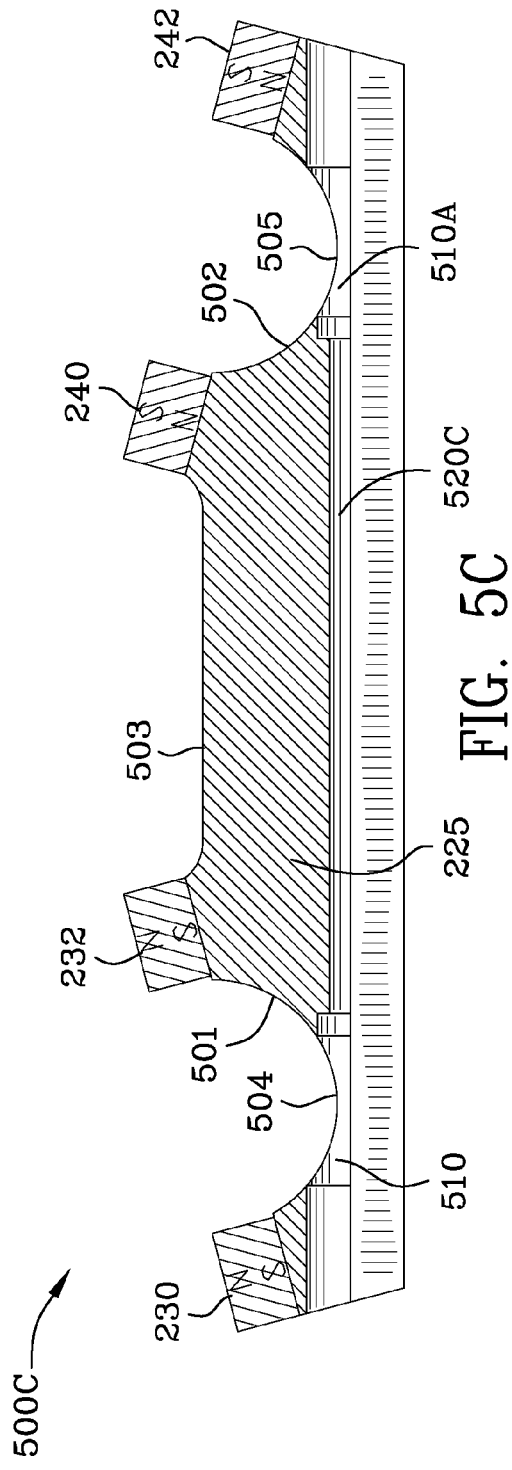

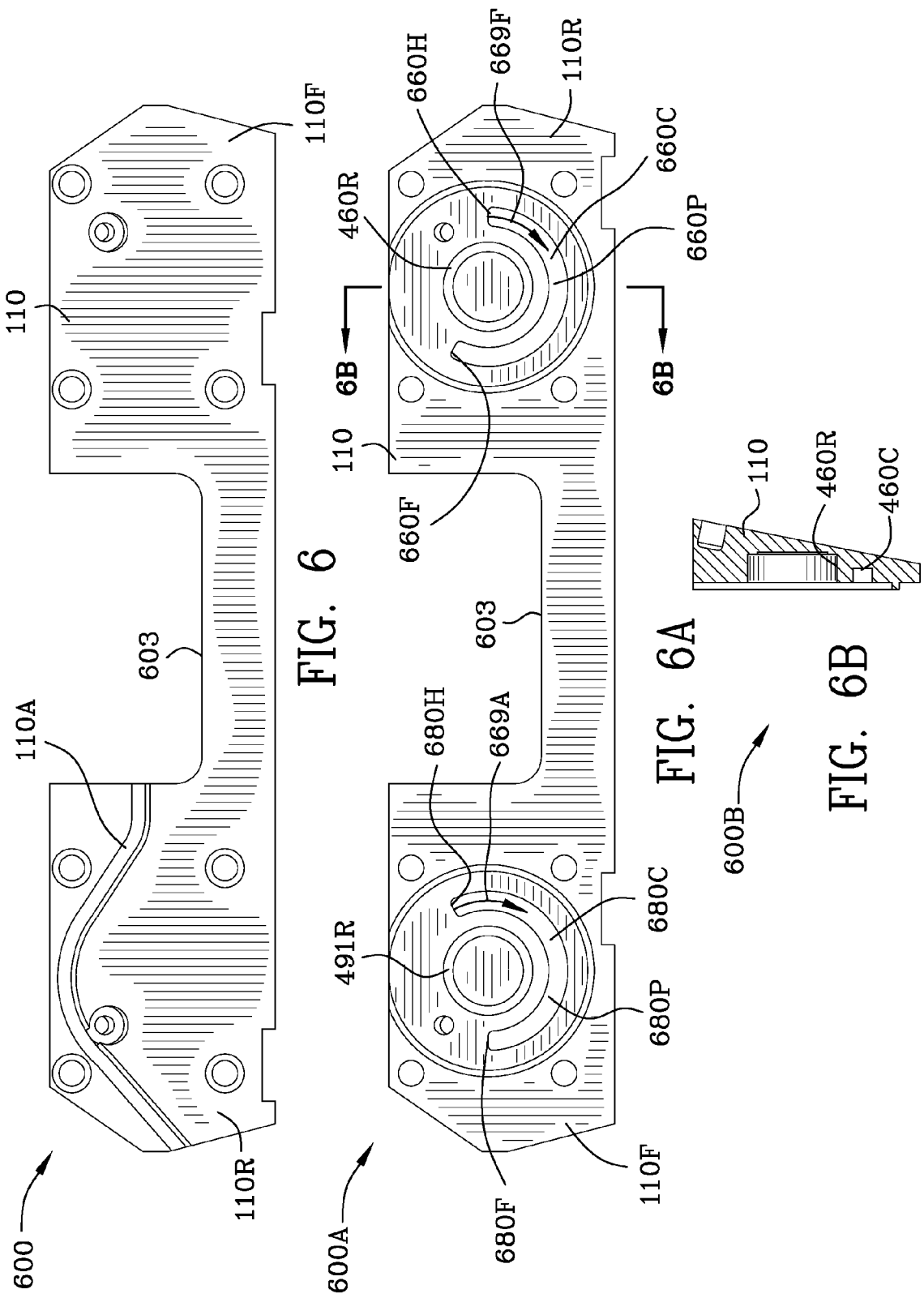

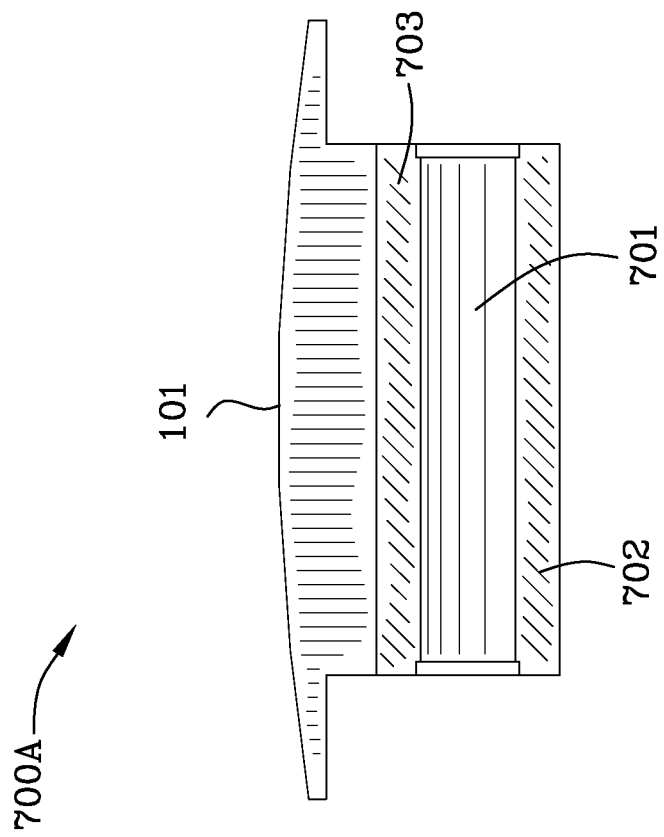
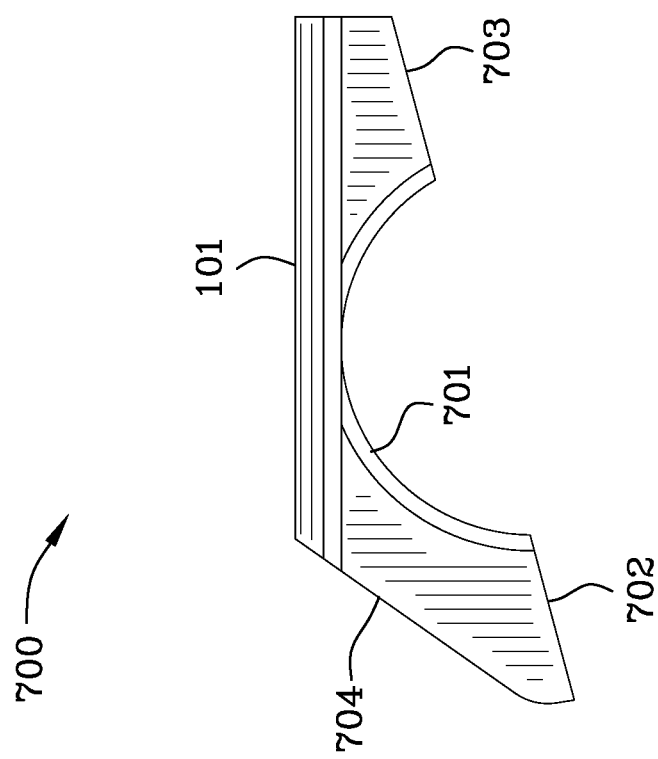

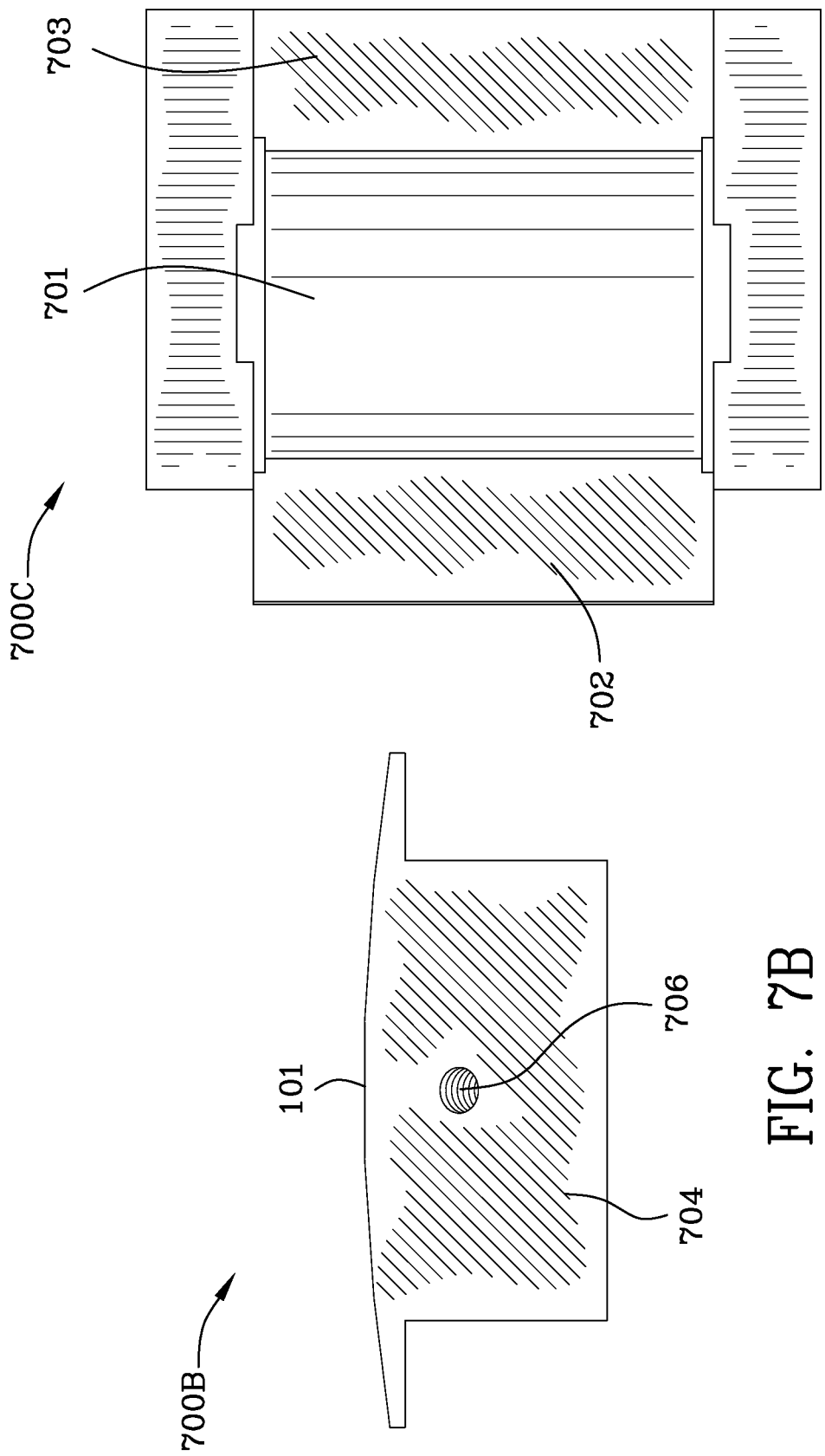

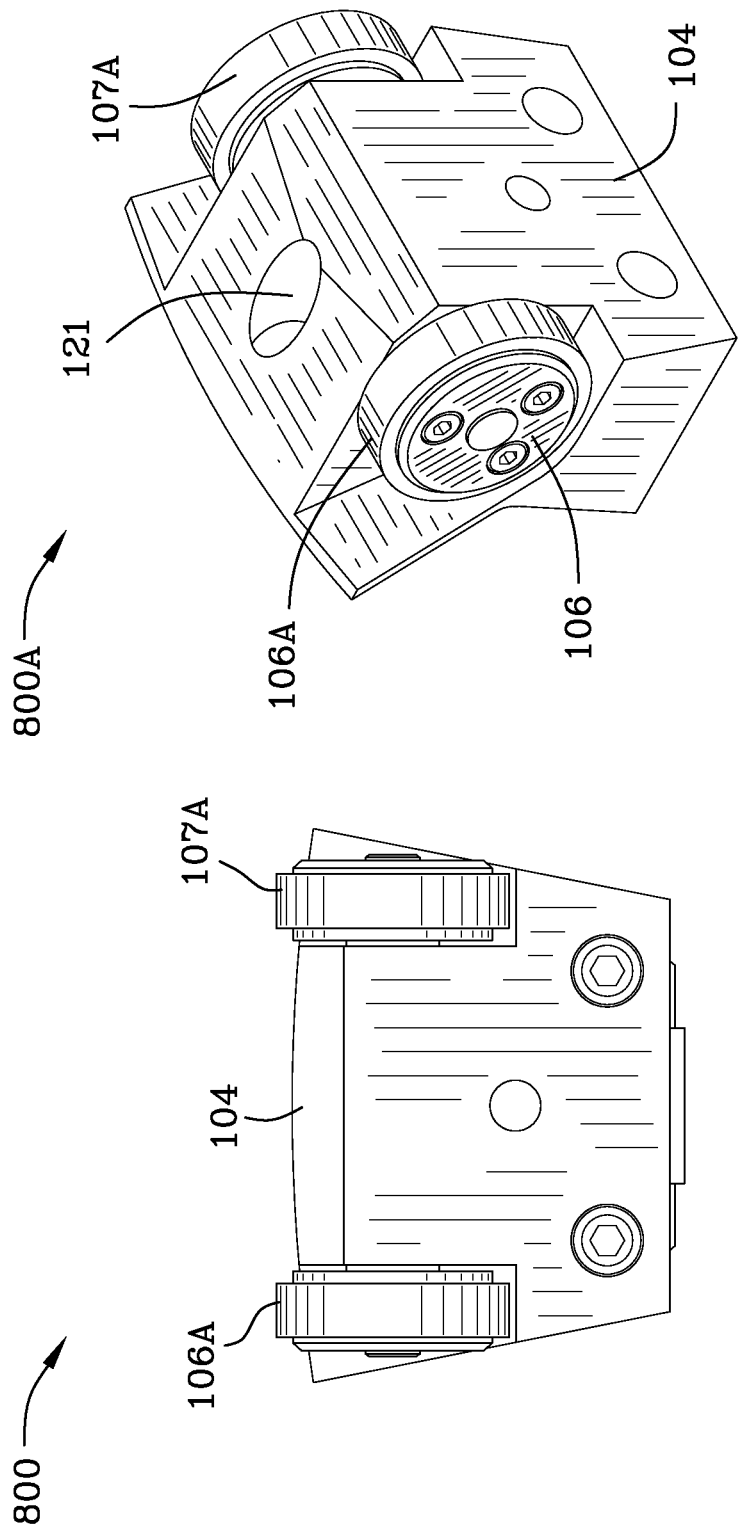

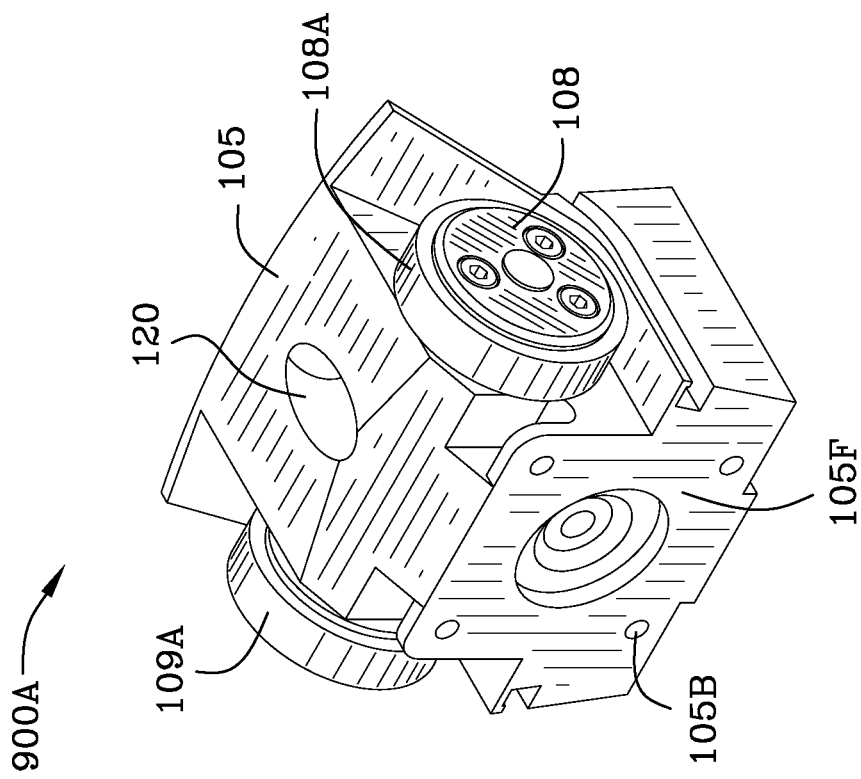
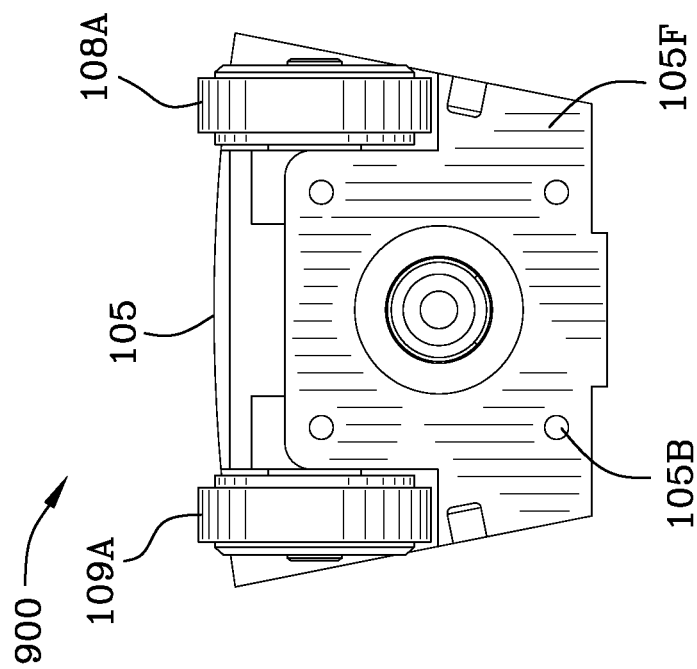
FIG. 9A
FIG. 9

CONDUIT SENSOR DEVICE WITH MAGNETIC SHUNT AND PROCESS FOR MODIFYING A MAGNETIC FIELD

This application is a continuation of copending U.S. patent application Ser. No. 12/836,230, filed Jul. 14, 2010, and this application claims the benefit and priority of and to U.S. patent application Ser. No. 12/836,230, filed Jul. 14, 2010 and the same is incorporated herein in its entirety by reference hereto.

FIELD OF THE INVENTION

The invention is in the field of pipeline inspection devices/sensors.

BACKGROUND OF THE INVENTION

U.S. Pat. No. 6,762,602 to Laursen et al. proposed a "device, e.g. an inspection pig, for inspecting conduits made from ferromagnetic materials, such as pipelines, for faults, cracks, corrosion or the like, comprising at least one pulling element, a supporting structure of variable circumference, disposed on the pulling element and comprising substantially radially disposed supporting arms each of which is pivotable about axes disposed perpendicular to the longitudinal central axis of the pulling element, and several permanent magnets disposed at the circumference of the supporting structure for generating a magnetic filed, and with sensors." Further, Laursen, states: "[f] or strengthening or weakening the magnetic field generated by the permanent magnet in dependence on the circumference of the supporting structure or in dependence on the lateral separation between the permanent magnets. The permanent magnets are associated with further magnets having a magnetic field which can be varied in direction or strength. In an embodiment, the further magnets associated with the permanent magnets are permanent magnets, wherein the direction of their magnetic field can be changed by turning using an electric or mechanical actuator. In another embodiment coils are used as magnets, which can be supplied with a variable current." See, the Abstract of U.S. Pat. No. 6,762,602 to Laursen et al.

The diametrical size of the conduit, the thickness of the conduit, and the lateral separation of the poles of the magnet are factors in the performance of the sensor. Sensors such as piezo-electric, electro-acoustic, and electromagnetic sensors such as Hall, stray flux and eddy current sensors may be used.

U.S. Pat. No. 6,762,602 to Laursen et al. does not effectively shunt the magnetic field produced by the poles through use of respective rotatable magnets. Additionally, the drive system of the rotatable magnets disclosed in U.S. Pat. No. 6,762,602 to Laursen et al. involves a mechanical system using springs and a toothed wheel with a selected diameter and selected number of teeth. The diameter and the number of teeth may be changed to control the rotatable magnet. Further, a spring is necessary for each of the rotatable magnets and adjustment of those magnets in a coordinated manner is difficult, and, therefore, control of the magnetic field is difficult. One of the poles in the Laursen '602 patent may be adjusted differently than the other pole because the springs and toothed gears cannot be matched or properly controlled. Spring constants and biasing of the rotatable magnets in Laursen et al. may not be equal and, hence, contribution of each of the poles to the magnetic field may be different.

Alternatively, U.S. Pat. No. 6,762,602 to Laursen et al., further discloses an electrically driven toothed wheel which is controlled by appropriate electric, electronic or mechanical sensor element for determining the lateral separation between the parallelogram supports. However, there is no disclosure in Laursen as to the coordinated operation and control of the rotatable magnets.

A more effective magnetic shunt which substantially completely reduces the magnetic field associated with a plurality of inner peripheral sensors is needed for unpiggable pipe lines. So-called unpiggable pipe lines require substantial cancellation of the magnetic field caused by permanent magnets used in conduit sensors placed in proximity to the conduit/pipe line. When the field created by the permanent magnets is substantially cancelled, the sensor may be drawn more easily through the pipeline as the sensor and its supporting structure are no longer magnetically attracted to the walls of the conduit/pipeline.

Use of a conduit sensor device requires application of north and south poles in proximity to the conduit/pipe line wall which creates a magnetic field extending into the wall of the conduit/pipe line. Control of the magnetic field which enters the conduit/pipe line is necessary for the correct interpretation of data obtained from the sensors. Sensors, such as a Hall effect sensors, measure anomalies such as cracks and deterioration of the structure of the conduit/pipeline when a magnetic field is imparted in the conduit/pipeline. Control of the magnetic field imparted in the conduit/pipeline is important as it allows correct interpretation of the data generated from the sensors. As such, a conduit sensor device which accurately controls the magnetic field in the conduit/pipeline wall is needed.

SUMMARY OF THE INVENTION

There are a plurality of conduit sensor devices arranged on the inner periphery of the pipeline/conduit which form an inspection pig. Each conduit sensor device includes several sensors associated therewith and each device covers a sector of the pipeline/conduit. Sixteen (more or less) conduit sensor devices may be used to cover the full inner surface of a cylindrically shaped pipeline/conduit. Any number of conduit sensors may be used to form an inspection pig.

Each conduit sensor device includes a magnetic shunt device. The magnetic shunt device is used effectively turns off the magnetic field. The inspection pig is propelled through the pipeline/conduit by drive means which are not shown. Each of the conduit sensor devices are connected to the drive means. Further, and importantly, the magnetic shunt device enables the curtailment of the magnetic field in the pipeline/conduit making movement of the inspection pig within the interior of the pipeline/conduit and through valves and other obstructions inside the pipeline easier. As stated above the inspection pig is driven by drive means not shown.

Further, the magnetic shunt device imparts an appropriately adjustable magnetic field into the pipeline/conduit as dictated by the operation of the inspection pig and/or as required for other reasons such as comparison of the data presently being taken against previously taken data for a given conduit/pipeline.

The conduit sensor device includes first and second pairs of permanent magnets. First and second rotor shunts include first and second rotatable magnets interposed between the first and second pairs of permanent magnets, respectively. A shunt shaft includes a first helical worm gear and a second helical worm gear mounted thereon. Both helical gears are right handed. The first rotor shunt includes a first rotatable magnet and a first rotor gear locked together. The first helical worm gear meshes with the first rotor gear driving the first rotor gear and the first rotatable magnet. The second rotor shunt includes a second rotatable magnet and a second rotor gear locked together. The second helical worm gear meshes with the second rotor gear driving the second rotor gear and the second rotatable magnet. The surface areas of the first pair of permanent magnets equals the surface area of the first rotatable magnet. Similarly, the surface areas of the second pair of permanent magnets equals the surface area of the second rotatable magnet.

The conduit sensor device includes an aft pole having includes an aft magnet set comprised of a first aft permanent magnet, a second aft permanent magnet, and a first rotatable magnet interposed between the first aft permanent magnet and the second aft permanent magnet. A forward pole includes a forward magnet set. The forward magnet set includes a first forward permanent magnet, a second permanent magnet, and a second rotatable magnet interposed between the first forward permanent magnet and the second permanent magnet. A sensor is interposed between the aft magnet set and the forward magnet set.

A backing bar supports the first aft permanent magnet, the second aft permanent magnet, the first forward permanent magnet, and the second forward permanent magnet. The first pole piece secures the first permanent magnet and the second permanent magnet to the backing bar. The second pole piece secures the first forward permanent magnet and the second permanent magnet to the backing bar.

A shunt shaft runs approximately the length of the device and includes an aft helical worm gear and a forward helical worm gear. Both worm gears are right handed helical gears. A first rotor worm gear meshes in engagement with the shaft driven device aft helical worm gear and a second rotor worm gear meshes in engagement with the shaft driven forward helical worm gear. The first rotatable magnet is in rotating engagement with the first rotor worm gear. The second rotatable magnet is in rotating engagement with the second rotor worm gear.

The first rotatable magnet includes a first half and a second half. The second rotatable magnet includes a first half and a second half. The first half of the first rotatable magnet and the second half of the first rotatable magnet are affixed to the first rotor worm gear. Similarly, the first half of the second rotatable magnet and the second half of the second rotatable magnet are affixed to the second rotor worm gear.

A bidirectional motor is coupled to the shunt shaft rotating the aft helical worm gear, the first rotor worm gear and the first rotatable magnet as well as the forward helical worm gear, the second rotor worm gear and the second rotatable magnet.

The first rotor shunt, the first rotatable magnet halves, the second rotor shunt and the second rotatable magnet halves are synchronously rotated and positioned. The shunt shaft is driven bidirectionally and the first and second rotor gears are driven bidirectionally and synchronously. The rotatable magnets mechanically coupled to the rotor gears rotate bidirectionally, in the same direction, and synchronously.

The conduit sensor assembly includes a first side keeper plate and a second side keeper plate. The first keeper plate includes a first arcuate slot and a second arcuate slot. The second keeper plate includes a first arcuate slot and a second arcuate slot. The first rotor shunt includes a first end trunion and a second end trunion. The first end trunion of the first rotor shunt includes a first protrusion and the second end trunion of the first rotor shunt includes a second protrusion. The protrusions of the first and second end trunions of the first rotor shunt reside in and are guided in the first arcuate slots, respectively, of the first and second keeper plates. The second rotor shunt includes a first end trunion and a second end trunion. The first end trunion of the second rotor shunt includes a first protrusion. The second end trunion of the second rotor shunt includes a second protrusion. The protrusions of the first and second end trunions of the second rotor shunt reside in and are guided in the second arcuate slots, respectively, of the first and second keeper plates.

The first arcuate slot of the first keeper plate extends 180° from a home position to a final position and the first arcuate slot of the second keeper plate extends 180° from a home position to a final position. The home positions and the final positions limit the travel of the protrusions/rotor shunts/rotatable magnets. Home and final positions are stops. The protrusion of the first end trunion of the first rotor shunt resides in the first arcuate slot of the first keeper plate and is movable between the home position and the final position of the first arcuate slot of the first keeper plate. The protrusion of the second end trunion of the first rotor shunt resides in the first arcuate slot of the second keeper plate and is movable between the home position and the final position of the first arcuate slot of the second keeper plate. The second arcuate slot of the first keeper plate extends 180° from a home position to a final position and the second arcuate slot of the second keeper plate extends 180° from a home position to a final position. The protrusion of the first end trunion of the second rotor shunt resides in the second arcuate slot of the first keeper plate and is movable between the home position and the final position of the second arcuate slot of the first keeper plate. The protrusion of the second end trunion of the second rotor shunt resides in the second arcuate slot of the second keeper plate and is movable between the home position and the final position of the second arcuate slot of the second keeper plate.

The first set of magnets form a first magnetic pole and the second set of magnets form a second magnetic pole. The first and second magnetic poles include a magnetic field therebetween which, when in use during an inspection, reside partially in the pipeline/conduit to be inspected. The first rotor gear is capable of rotating the first rotor shunt and the first rotatable magnet 180° from home position to final position. The second rotor gear, rotating synchronously with the first rotor gear, is capable of rotating the second rotor shunt and the second rotatable magnet 180°. The first and second rotatable magnets substantially cancel the magnetic field located between the first and the second magnetic poles when rotated to their final positions.

The first rotor gear rotates the first rotor shunt and the first rotatable magnet between 0° and 180° synchronously with the second rotor gear rotating the second rotor shunt and the second rotatable magnet between 0° to 180°. Positioning of the first and second rotatable magnets between the respective permanent magnets moderates the magnetic field located between the first and the second magnetic poles.

A stepper motor bidirectionally drives the shunt shaft, the helical worm gears, the rotor gears, the rotor shunts and the first and second rotatable magnets.

A process for modifying a magnetic field generated between magnetic poles with the magnetic field in proximity to a ferromagnetic conduit is disclosed and claimed. The process includes the steps of: (1) driving, bidirectionally, a shunt shaft having first and second helical gears; (2) rotating, using the first helical gear and a first rotor gear, a first rotor shunt residing intermediate a first set of permanent magnets forming a first magnetic pole, the first rotor shunt includes a first rotatable magnet rotating therewith; (3) synchronously rotating, using the second helical gear and a second rotor gear, a second rotor shunt residing intermediate a second set of permanent magnets forming a second magnetic pole, the second rotor shunt includes a second rotatable magnet rotating therewith; (4) discontinuing the rotation of the first rotor shunt and the second rotor shunt synchronously positioning the first rotatable magnet intermediate the first set of permanent magnets and the second rotatable magnet intermediate the second set of permanent magnets; and, (5) modifying the magnetic field generated between the magnet poles. The steps of: (1) rotating, using the first helical gear and a first rotor gear, a first rotor shunt residing intermediate a first set of permanent magnets forming a first magnetic pole, the first rotor shunt includes a first rotatable magnet rotating therewith, and, (3) synchronously rotating, using the second helical gear and a second rotor gear, a second rotor shunt residing intermediate a second set of permanent magnets forming a second magnetic pole, the second rotor shunt includes a second rotatable magnet rotating therewith; include rotating the first and second shunt rotors between 0° and 180°, the first and second rotatable magnets rotating therewith, respectively.

The process may be performed with a first rotor shunt which includes a protrusion extending therefrom and second rotor shunt which includes a protrusion extending therefrom. The process includes the further step of: guiding and interengaging the protrusion of the first rotor shunt in a first arcuate slot in a side wall. The first arcuate slot extending between 0° and 180°. The process further includes the step of guiding and interengaging the protrusion of the second rotor shunt in a second slot in a side wall. The second arcuate slot extending between 0° and 180°.

One of the features of the process for modifying a magnetic field generated between magnetic poles includes cancelling the magnetic field when the rotation of the protrusions of the first and second rotor shunts are positioned in the first and second slots at 180°.

Another example of the conduit sensor device comprises first and second pairs of permanent magnets. The first pair of permanent magnets includes a first magnet and a second magnet. The first and second magnets include outer surfaces, the outer surfaces of the first magnet have a first area and the outer surfaces of the second magnet have a second area. The second pair of permanent magnets includes a fifth magnet and a sixth magnet and the fifth and the sixth magnets include outer surfaces.

The outer surfaces of the fifth magnet have a fifth area and the outer surfaces of the sixth magnet have a sixth area. A first rotor shunt is interposed between the first pair of permanent magnets and a second rotor shunt is interposed between the second pair of permanent magnets. A shunt shaft runs the length of the device and includes a first helical worm gear and a second helical worm gear mounted thereon. The first rotor shunt includes a first rotatable magnet and a first rotor gear and the first rotatable magnet and the first rotor gear are locked together such that the first rotatable magnet rotates with the first rotor gear. The first helical worm gear meshes with the first rotor gear and drives the first rotor gear and the first rotatable magnet. The second rotor shunt includes a second rotatable magnet and a second rotor gear. The second rotatable magnet and the second rotor gear are locked together such that the second rotatable magnet rotates with the second rotor gear. The second helical worm gear meshes with the second rotor gear and drives the second rotor gear and the second rotatable magnet. The first rotatable magnet is comprised of a third and fourth magnet. The third and fourth rotatable magnets include outer surfaces, the outer surface of the third magnet has a third area and the outer surface of the fourth magnet includes a fourth area. The second rotatable magnet is comprised of a seventh and eighth magnet. The seventh and eighth magnets include outer surfaces. The outer surface of the seventh magnet has a seventh area and the outer surface of the eighth magnet includes an eighth area. The area of the first magnet and the area of the second magnet, when combined, equal the combined area of the third and fourth magnets. The area of the fifth magnet and the area of the sixth magnet, when combined, equal the combined area of the fifth and sixth magnets. The first rotatable magnet and the second rotatable magnet are synchronously rotated and positioned.

It is an object of the invention to substantially completely reduce the magnetic field for use in so-called unpiggable pipe lines.

It is a further object of the invention to substantially cancel the magnetic field between the poles of the device so that the device may be drawn more easily through the pipeline as the sensor and its supporting structure are no longer magnetically attracted to the walls of the conduit/pipeline.

It is a further object of the invention to control the magnitude of the magnetic field which enters the conduit/pipe line.

It is a further object of the invention to control the magnetic field imparted in the conduit/pipeline to allow correct interpretation of the data generated from the sensors.

It is a further object of the invention to control the magnetic field in the conduit/pipeline wall for a wide variety of pipe diameters and for a wide variety of pipe thicknesses.

It is a further object of the invention to synchronously control the magnetic field created by the aft and forward magnetic poles of the pipeline inspection device.

It is a further object of the invention to mechanically prevent the over travel of the rotor shunts and the rotatable magnets of the pipeline inspection device.

It is a further object of the invention to substantially cancel the entire magnetic field of the pipeline inspection device to enable negotiation within the conduit/pipeline.

It is a further object of the invention to cancel a portion of the magnetic field of the pipeline inspection device to enable use of the pipeline inspection device in different environments.

It is a further object of the invention to provide rotor shunts having magnets rotating therewith between 0°-180° for modifying and/or cancelling the magnetic field between two magnetic poles.

These and other objects will be best understood when reference is made to the drawings and the description of the invention set forth below.

It is a further object of the invention to synchronously position the aft and forward rotatable magnets.

It is a further object of the invention to precisely and simultaneously position the aft and forward rotatable magnets.

It is a further object of the invention to use rare earth permanent magnets.

It is a further object of the invention to use rare earth rotatable magnets.

It is a further object of the invention to use 1008 steel as the material for the backing bar.

BRIEF DESCRIPTION OF THE DRAWINGS

FIG. 1B is a top view of the conduit sensor device which includes a magnetic shunt device.

FIG. 1C is a side view of the conduit sensor device.

FIG. 3 is a top view of the shunt shaft illustrating the aft and forward worms.

FIG. 3A is a cross-sectional view of the shunt shaft taken along the lines 3A-3A of FIG. 3.

FIG. 4 is a perspective view of the aft rotor shunt.

FIG. 4A is an exploded perspective view of the aft rotor shunt.

FIG. 5 is a top view of the backing bar and fixed permanent magnets.

FIG. 5A is a side view of the backing bar and fixed permanent magnets.

FIG. 5B is a bottom view of the backing bar.

FIG. 5C is a cross-section view of the backing bar and fixed permanent magnets taken along the lines 5C-5C of the FIG. 5.

FIG. 6 illustrates the outside of the side keeper block of one side of the magnetic sensor shunt device.

FIG. 6A illustrates the inside of the side keeper block of FIG. 6.

FIG. 6B is a cross-sectional view taken along the lines 6B-6B of FIG. 6A.

FIG. 7 is a side view of the aft pole.

FIG. 7A is an end view of the aft pole.

FIG. 7B is a rear view of the aft pole.

FIG. 7C is a bottom view of the aft pole.

FIG. 8 is an end view of forward end block.

FIG. 8A is a perspective view of the forward end block.

FIG. 9 is an end view of the aft end block taken along the lines 9-9 of FIG. 1D.

FIG. 9A is a perspective view of the forward end block illustrating bolt holes for interconnection to the stepper motor.

DESCRIPTION OF THE INVENTION

Figure 1:
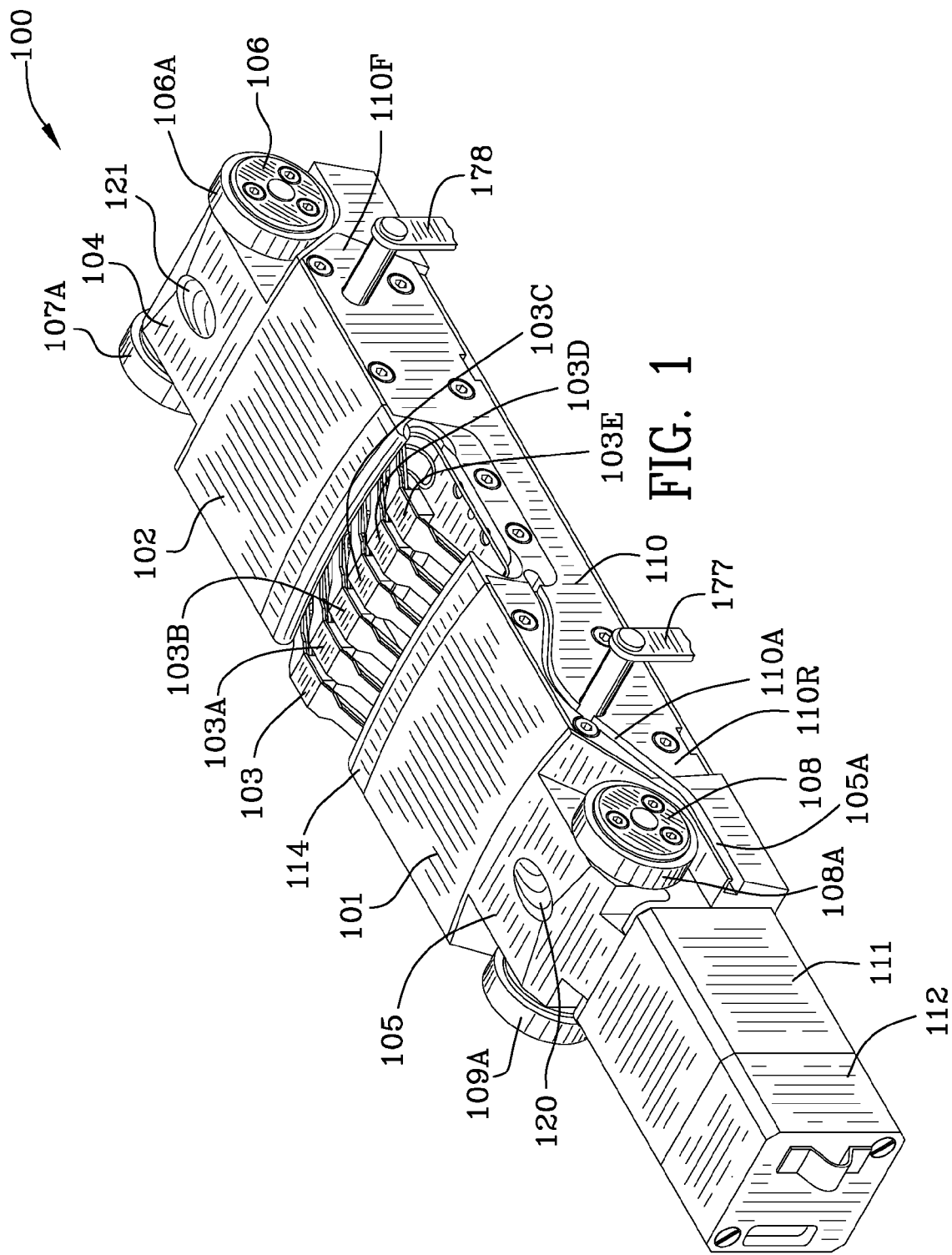
FIG. 1 is a perspective view of the conduit sensor device which includes a magnetic shunt device.

FIG. 1 is a perspective view 100 of the conduit sensor device including a magnetic shunt illustrating the aft pole 101, the forward pole 102, and sensors 103, 103A, 103B, 103C, 103D, 103E for detecting anomalies or variations in a conduit/pipeline. The conduit sensor which includes the magnetic shunt device shown and described herein is one of a plurality of such devices located about the inner periphery of the pipeline/conduit.

Poles 101, 102 are manufactured from 1018 steel. A magnetic field is created by sets of magnets beneath poles 101, 102. A first set (aft set) of magnets comprises rare earth permanent magnets 230, 232 and rare earth rotatable magnets 231, 271. A second set of magnets comprises rare earth magnets 240, 242 and rare earth rotatable magnets 241, 281. The rare earth magnets are NdFeB magnets. Other rare earth magnets may be used. Magnets other than rare earth magnets may be used. The device 100 is capable of modifying and/or substantially cancelling the magnetic field between the poles so as to facilitate propulsion of the device and the propelling mechanism (not shown) through the pipeline/conduit. When the poles are active and a magnetic field exists therebetween, the field interacts with a ferromagnetic pipeline and is attracted to said ferromagnetic pipeline.

The poles 101, 102 and backing bar 225 are the only components that should be made of ferrous materials. All other components such as side plates, end blocks, shunt shaft 301, shunt rotors, etc. are preferably made of non-ferrous material such as aluminum or brass or similar material. This is to maximize the amount of magnetic energy going into the pipeline/conduit wall 252, poles 101, 102, and backing bar 225 instead of going into the side plates 110, 113, end blocks 104, 105, shunt shaft 301, rotor gears 302G, 303G and other components.

Figure 1A:
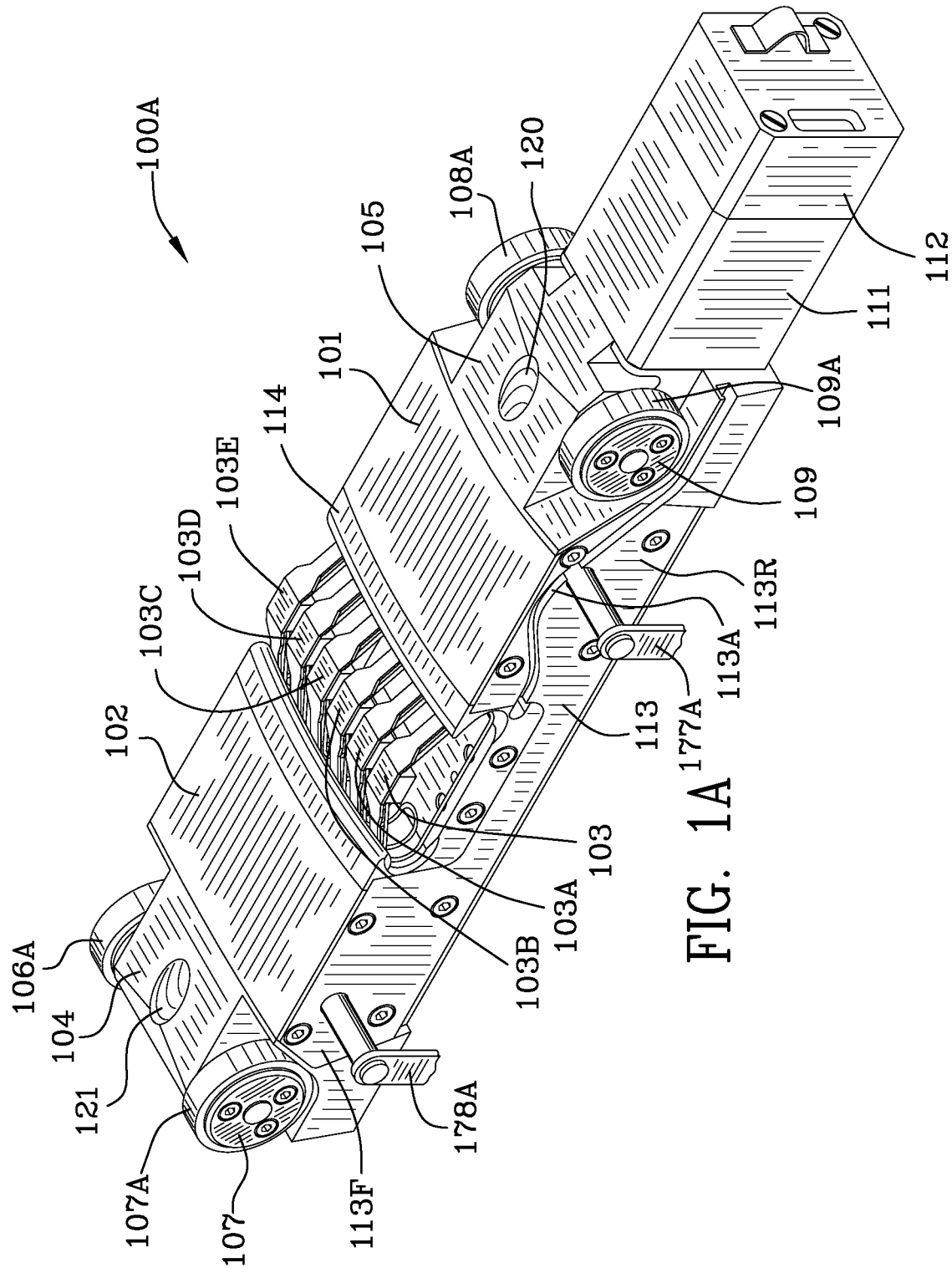
FIG. 1A is another perspective view of the conduit sensor device which includes a magnetic shunt device.

Forward end block 104 and aft (rear) end block 105 are illustrated in the perspective view of FIG. 1 as is the wire groove 105A in the aft end block 105. Forward end block 104 and aft end block 105 are secured to backing bar 225 illustrated in FIG. 2 by threaded studs (not shown). Wheels 106, 107, 108, 109 and corresponding rubber grips or tires 106A, 107A, 108A, 109A therefor are illustrated in FIG. 1A. The rubber grips engage the inner wall of a pipeline/conduit when the device performs an inspection. See FIG. 2C which illustrates pipeline/conduit 252. Side plate 110 and wire groove 110A in the side plate 110 are illustrated in the rearward (aft) portion of side plate 110. Further, the forward portion 110F of the side plate is illustrated in FIG. 1A. Generally, the terms aft and forward are used for points of reference herein. Aft is used to indicate the backward portion nearer stepper motor 111 and the controls/communication interface 112 for stepper motor 111. Forward is used to indicate the front portion opposite the stepper motor 111 and the control interface 112.

Support arms 177, 177A, 178, 178A support the conduit sensor device and extend and attach to the central propelling mechanism (not shown) of the inspection pig (device). The inspection pig (device) drives the plurality of conduit sensors through the pipeline/conduit using a drive means (not shown). Saddle 114 supports the sensors 103A-E. Bolt holes 120, 121 enable poles 101, 102 to secure be secured to the backing bar 225 as illustrated in FIG. 2.

FIG. 1A is another perspective view 100A of the conduit sensor device which includes the magnetic shunt device illustrating the side keeper plate 113 and the wire groove 113A therein. Reference numeral 113R denotes the rearward portion of the device in FIG. 1A and reference numeral 11F denotes the forward portion of the device in FIG. 1A. Wire grooves 110A, 113A enable routing of wires to the sensors 103A-E. Sensors 103A-E may be any type of electronic sensors including, for example, Hall effect sensors which detect anomalies/faults in the wall of the pipeline/conduit.

Figure 1D:
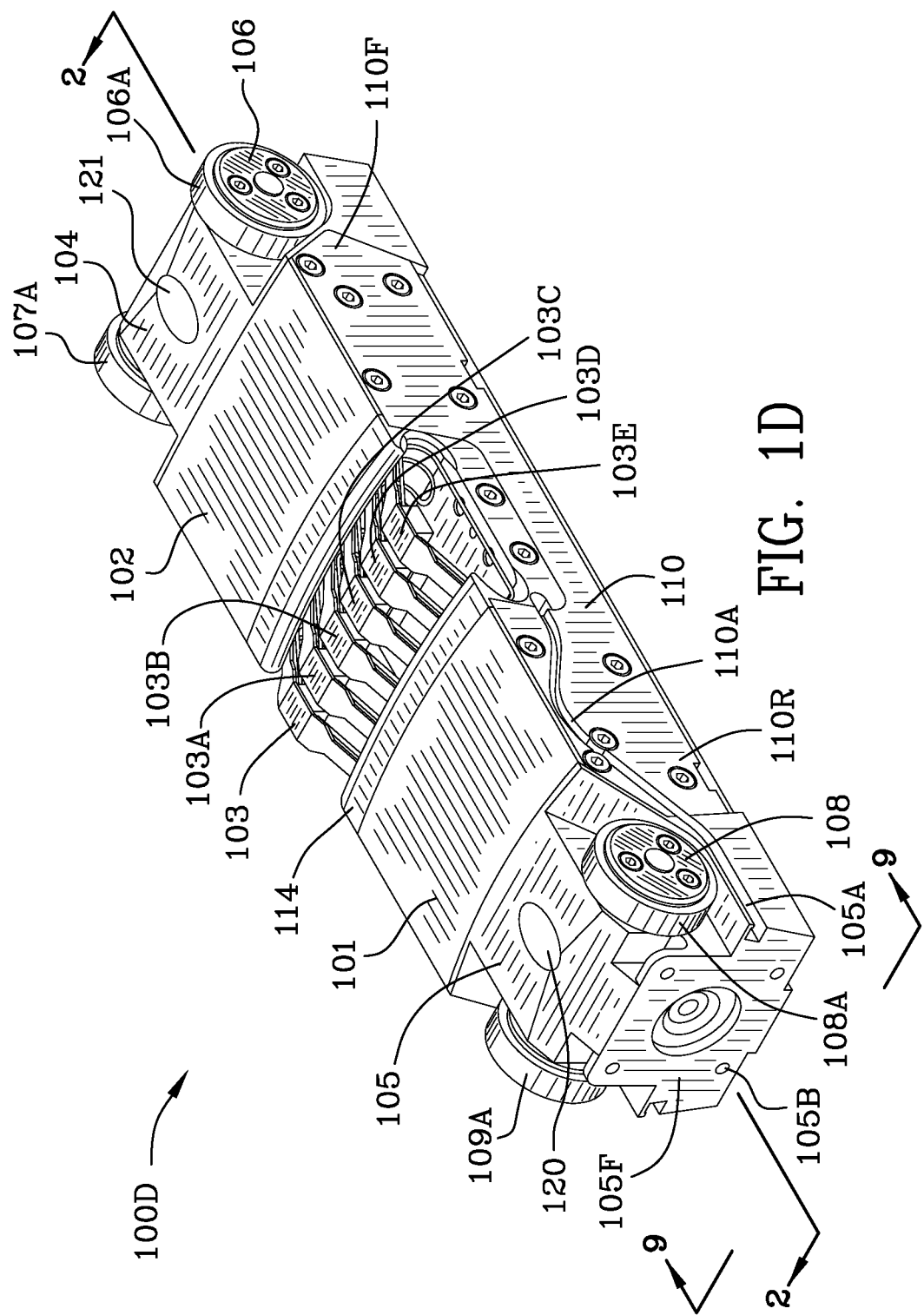
FIG. 1D is a perspective view of the conduit sensor device which includes the magnetic shunt device without the drive motor attached thereto.

FIG. 1B is a top view 100B of the conduit sensor device which includes the magnetic shunt device and FIG. 1C is a side view 100C of the conduit sensor device which includes the magnetic shunt device. FIG. 1D is a perspective view 100D of the conduit sensor device which includes the magnetic shunt device without the drive motor attached thereto. Rear end block 105 is illustrated in FIG. 1D along with bolt holes 105B for attachment to stepper motor 111. Also shown is flat face 105F which abuts stepper motor 111 when it is attached.

Figure 2:
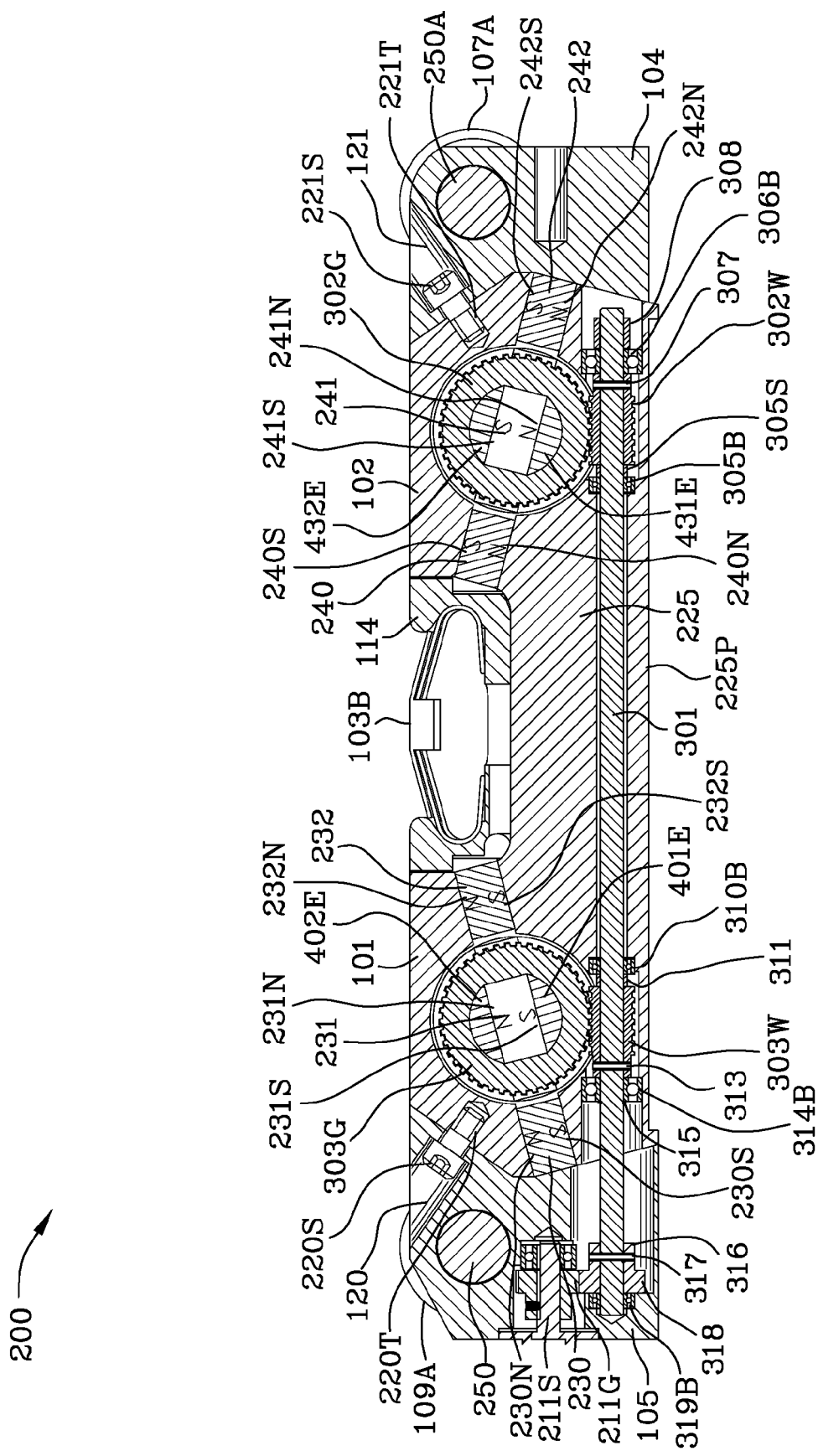
FIG. 2 is a cross-sectional view of the conduit sensor device which includes a magnetic shunt device taken along the lines 2-2 of FIG. 1B.

FIG. 2 is a cross-sectional view 200 of the conduit sensor device including the magnetic shunt device taken along the lines 2-2 of FIG. 1B illustrating input shaft 211S driving input gear 211G. Input shaft 211S is driven by stepper motor 111 not shown in FIG. 2. Screw 220S interengages bolt hole 120 and is threadedly connected to pole 101 which secures first aft permanent magnet 230 and second aft permanent magnet 232 of the aft magnet set to the backing bar 225. End blocks 104, 105 are secured to backing bar 225 through threaded connections which are not shown. End blocks 104, 105 are affixed to the backing bar 225 and screws 220S, 221S affix poles 101, 102 to the end blocks. Permanent magnets 230, 232, 240 and 242 are mechanically clamped into engagement with the poles 101, 102 and the backing bar 225. Reference numerals 220T, 221T represent the threaded interengagement of the screws 220S, 221S and the backing bar 225.

Backing bar 225 includes a shunt shaft channel 520C best viewed in FIG. 5C. FIG. 5C is a cross-section view 500C of the backing bar 225 and fixed permanent magnets 230, 232, 240, 242 taken along the lines 5C-5C of the FIG. 5. Gear 318 is affixed to shunt shaft 301 with a set screw 317. Gear 316 include gear teeth 318 which drive shunt shaft 301 as illustrated in FIGS. 2 and 3. Shunt shaft 301 is supported by: bearings 319B mounted in the aft housing 105, bearings 314B mounted in the backing bar 225/shaft support plate 225P, bearings 310B mounted in the backing bar 225/shaft support plate 225P, bearings 305B mounted in the backing bar 225/shaft support plate and bearings 306B in the backing bar 225/shaft support plate 225P. Aft helical worm gear 303W and forward helical worm gear 302W are mounted to shaft 301 and drive rotor gears 303G and 302G, respectively. Helical gear 302W is pinned 313 to shaft 301. Spacer 311 separates helical gear 303W from bearing 310B. Helical gear 303W resides between bearings 314B and 310B. Snap ring 315 secure bearings 314B from leftward lateral movement as illustrated in FIG. 2. Similarly, forward helical gear 302W is secured to shunt shaft 301 by pin 307. Spacer 305S separates bearing 305B from the helical gear 303W. Bearing 306B abuts forward helical gear 302W and is secured against rightward lateral movement when viewing FIG. 2 by collar 303 which is press-fit on shaft 301.

Still referring to FIG. 2, permanent magnet 230 includes north 230N and south 230S poles and permanent magnet 232 includes north 232N and south 232S poles. Rotatable magnet 231 is shown as being solid in FIG. 2 as the section line 2-2 is taken along the lines 2-2 of FIG. 1D. Section lines 2-2 are coincident with the end surface of rotatable magnet 231. Rotatable magnet 231 includes north 231N and south 231S poles. The aft rotatable magnet 231 is actually one-half of the aft rotatable magnet and reference is made to FIG. 4A for an illustration of the aft rotatable magnet halves 231, 271. The aft rotatable magnet is described herein as including a first half 231 and a second half 271. Rotor gear 303G in combination with the male magnet backers 401M, 402M, female magnet backers 401F, 402F, end trunions 460, 471 and screws 473, 474, 463, 464 as illustrated in FIG. 4A secure the first half 231 and second half 271 of the rotatable magnet together to form essentially one rotatable magnets.

Figure 4C:
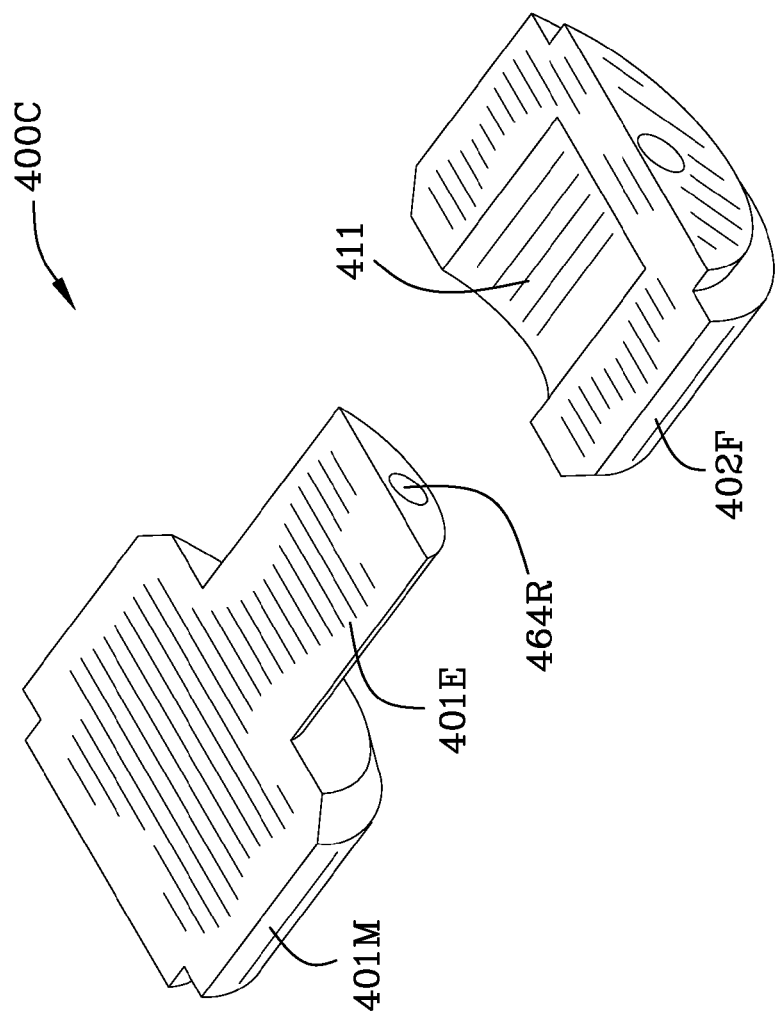
FIG. 4C is a perspective view of one set of male and female rotor backs of the aft rotor shunt.
Figure 4B:
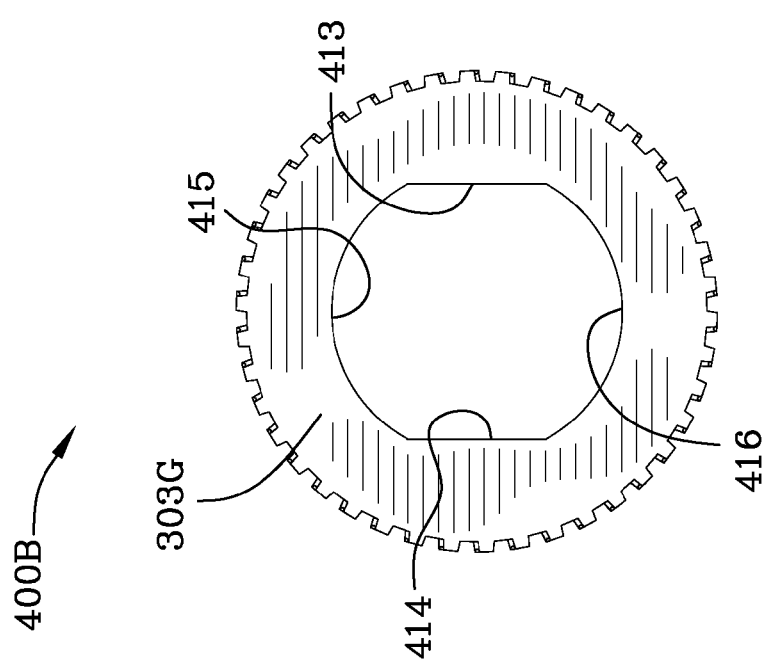
FIG. 4B is a front view of the aft rotor.

Still referring FIG. 2, permanent magnet 240 includes north 240N and south 240S poles and permanent magnet 242 includes north 242N and south 240S poles. Forward rotatable magnet 241 is shown solid in FIG. 2 as the section line 2-2 is taken along the lines 2-2 of FIG. 1D. As illustrated in FIGS. 4E and 4I, the forward rotatable magnet is one half of the forward rotatable magnet set 241, 281. Rotatable magnet half 241 includes a north pole 241N and a south pole 241S.

Figure 4D:
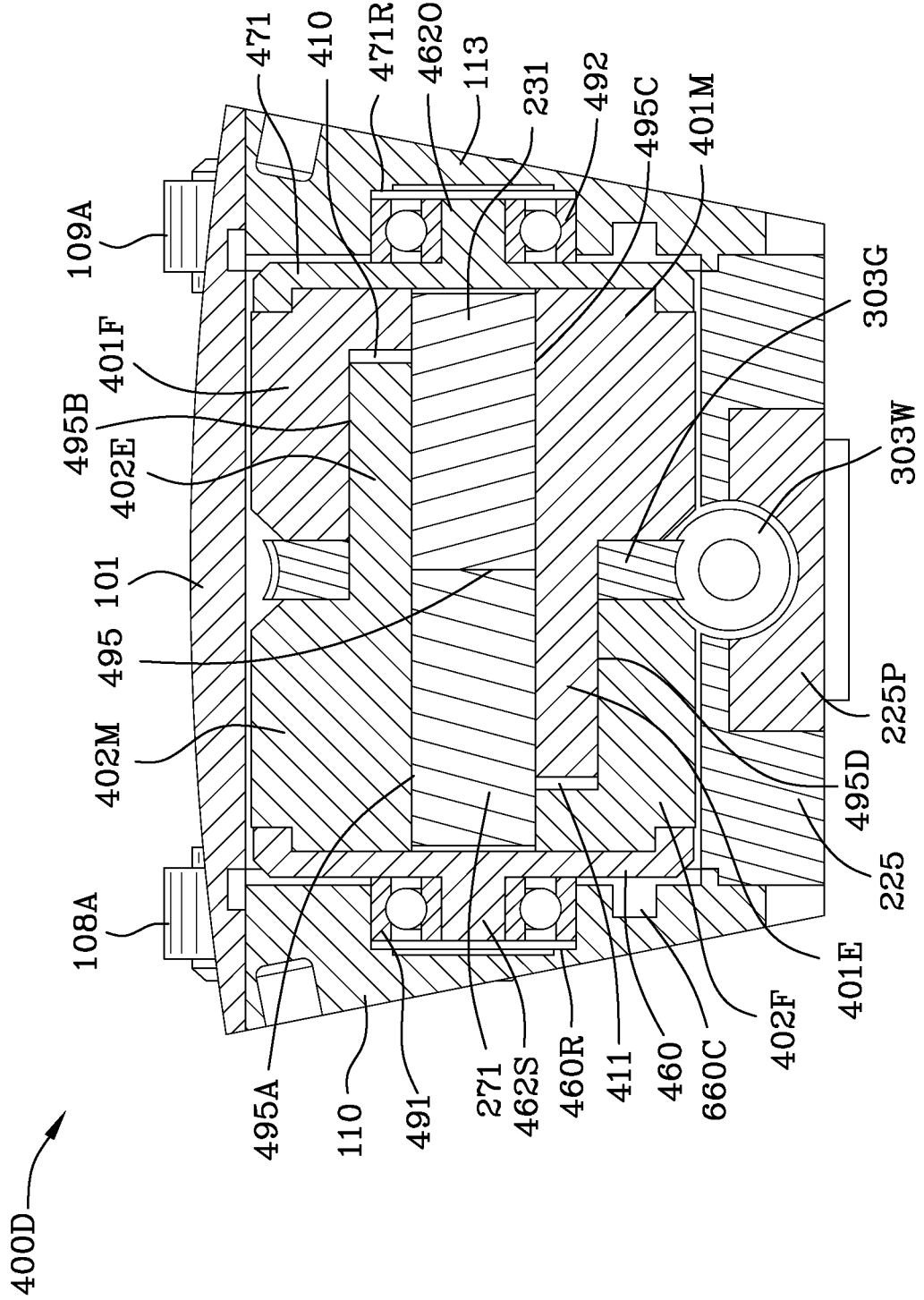
FIG. 4D is a cross-sectional view taken along the lines 4B-4B of FIG. 1C.
Figures 4E, 4F:
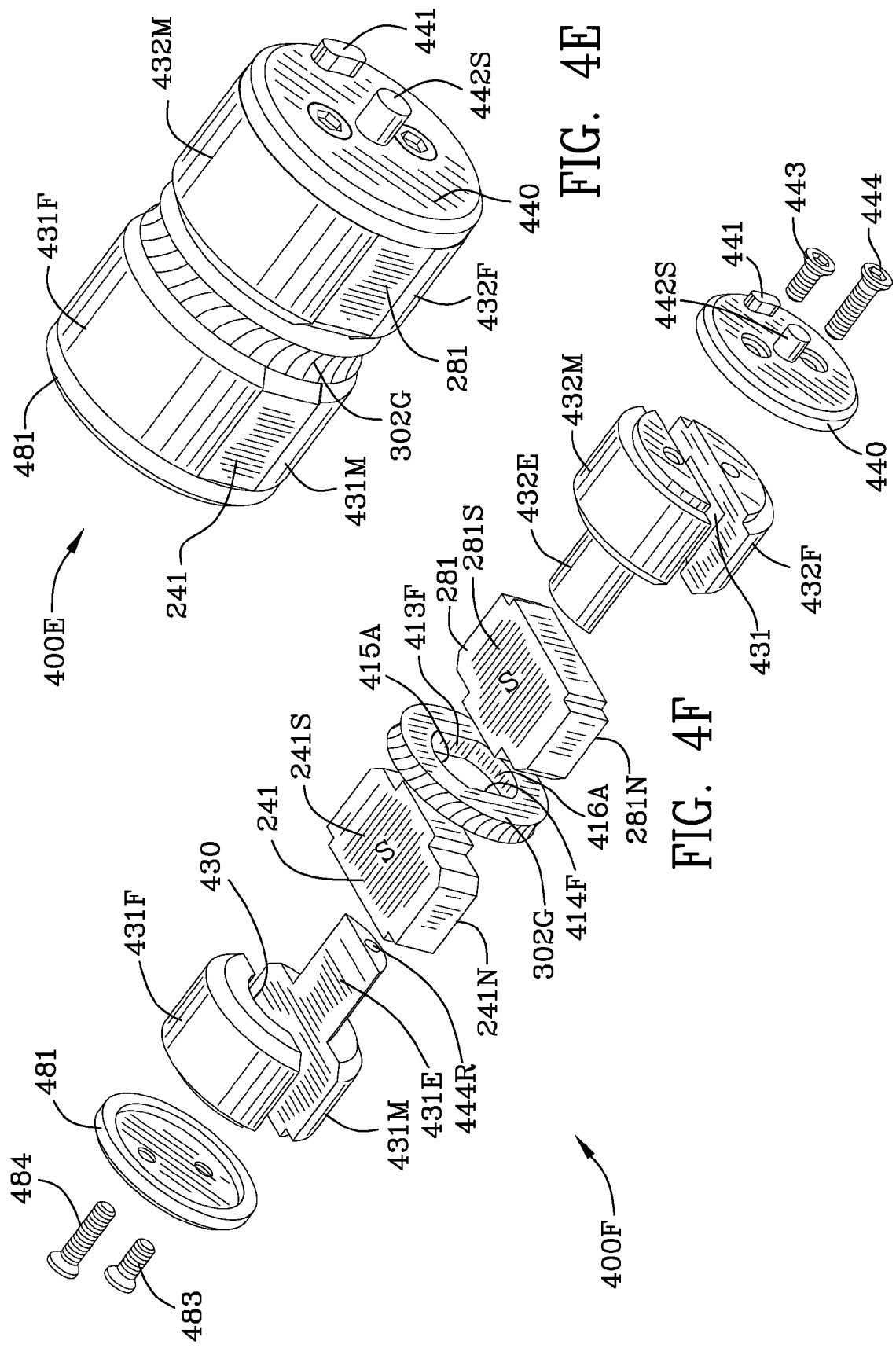
FIG. 4E is a perspective view of the forward rotor shunt.
FIG. 4F is an exploded perspective view of the forward rotor shunt.

Still referring to the aft rotor shunt and FIGS. 2, 4A, and 4D magnet backer extensions 402E and 401E interfit the interior of the rotor gear 303G and secure magnets 231, 271 in place. Rotatable magnets halves 231, 271 also interfit the interior of rotor gear 303G as viewed in FIGS. 2, 4A, and 4D. Similarly, referring to the forward rotor shunt and FIGS. 2, 4F, and 4G magnet backer extensions 432E, 431E secure forward magnet halves 241, 281 in place. Rotatable magnet halves 241, 281 also interfit the interior of rotor gear 302G as viewed in FIGS. 2, 4F, and 4G. Wheel shafts 250, 250A for wheels 106, 107, 108 and 109 are illustrated in FIG. 2 in cross-section.

Figure 2A:
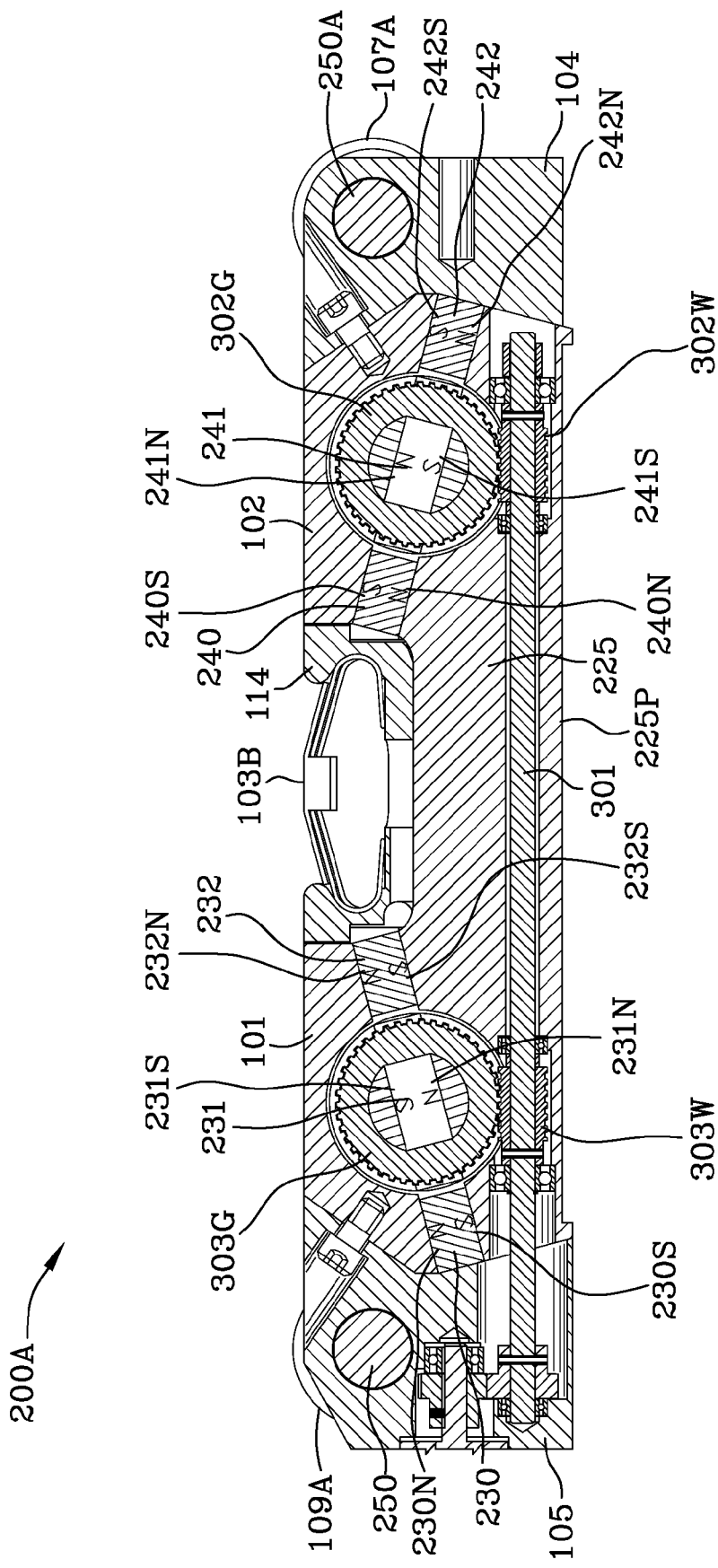
FIG. 2A is a cross-sectional view of the conduit sensor device which includes the magnetic shunt device taken along the lines 2-2 of FIG. 1B with the rotatable shunting magnets rotated 180° from their initial, home, positions.
Figure 2B:
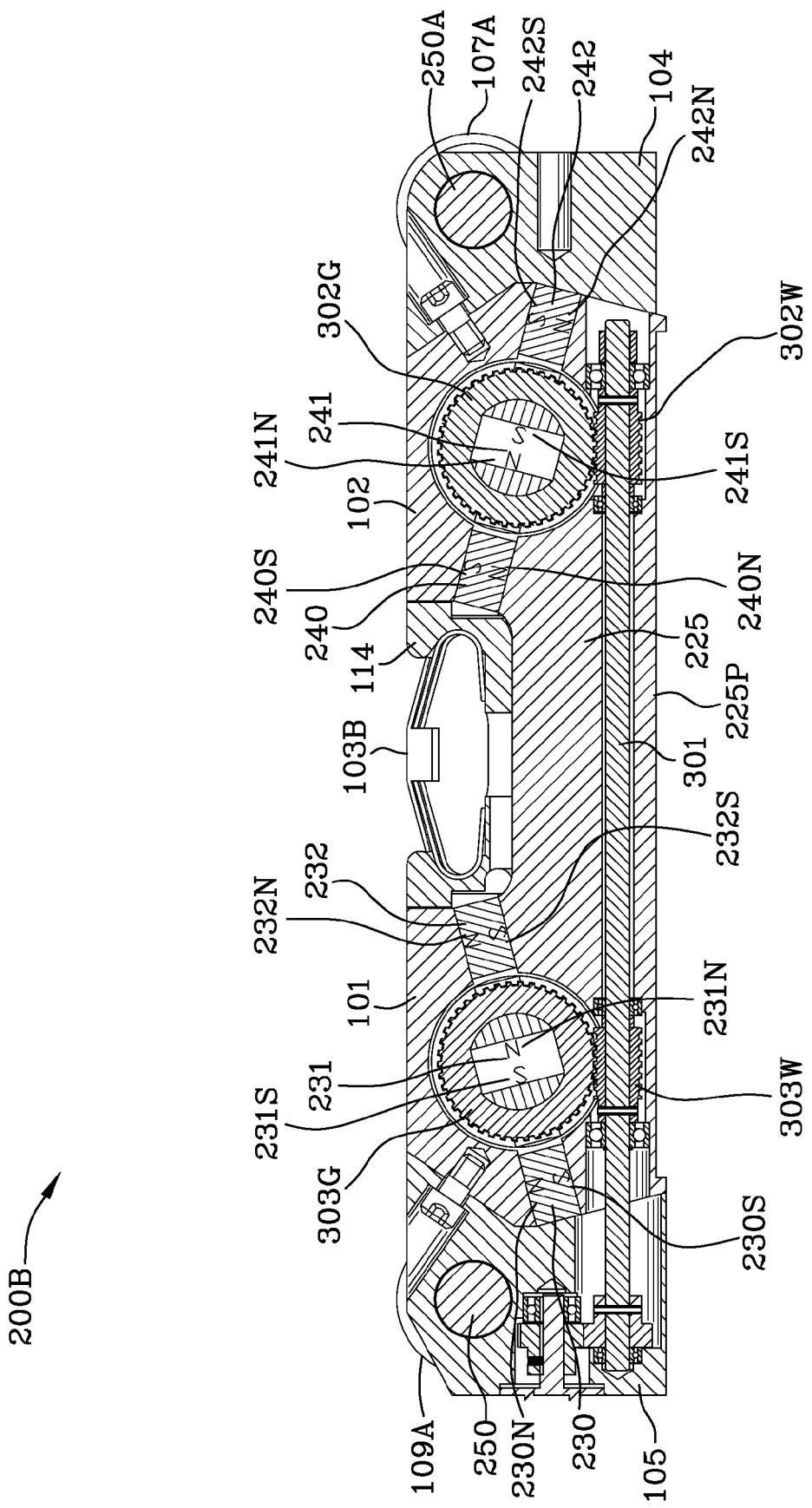
FIG. 2B is a cross-sectional view of the conduit sensor device which includes the magnetic sensor shunt device taken along the lines 2-2 of FIG. 1B with the rotatable shunting magnet rotated 90° from their initial, home, positions.
Figure 2C:
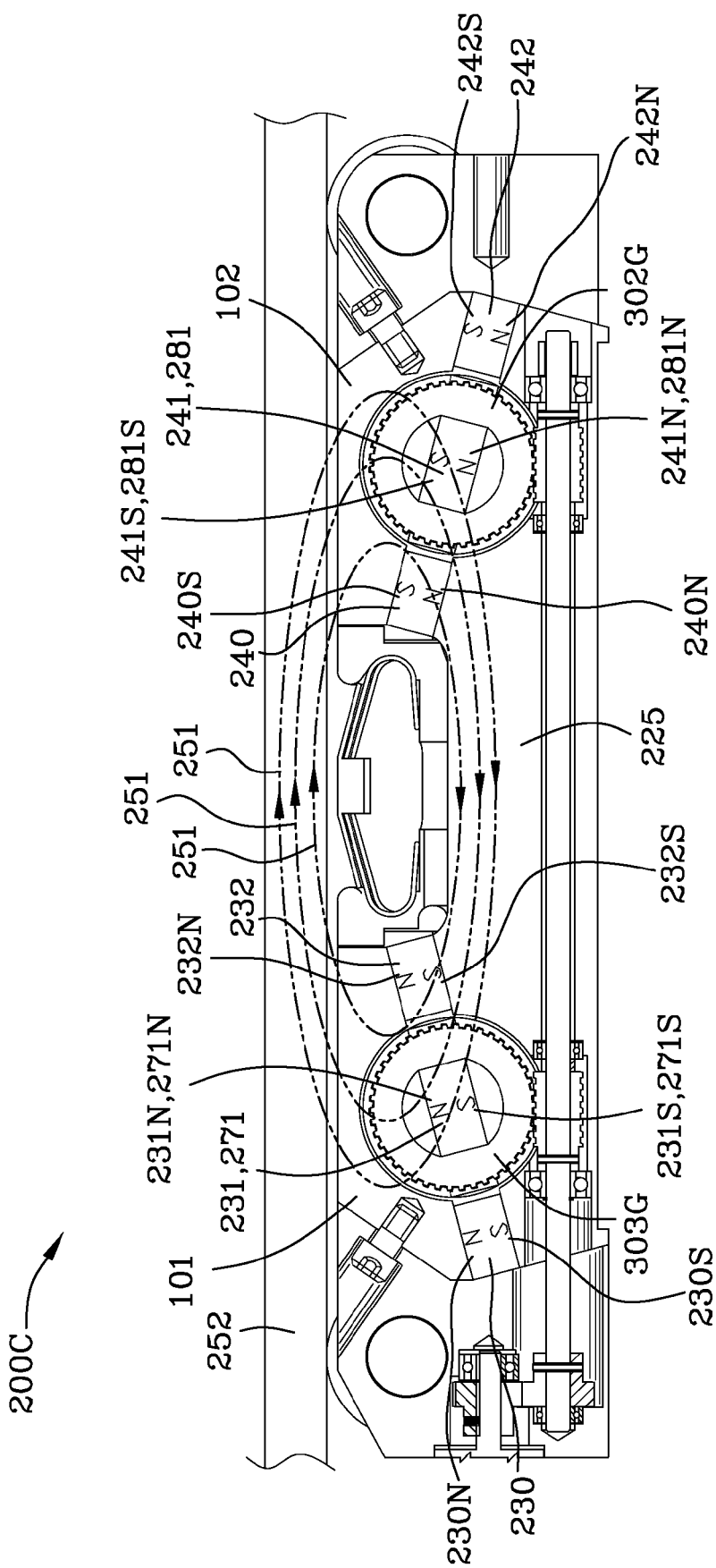
FIG. 2C is a schematic cross-sectional view of the conduit sensor device which includes the magnetic sensor shunt device similar to FIG. 2 with magnetic field lines illustrated.
Figure 2D:
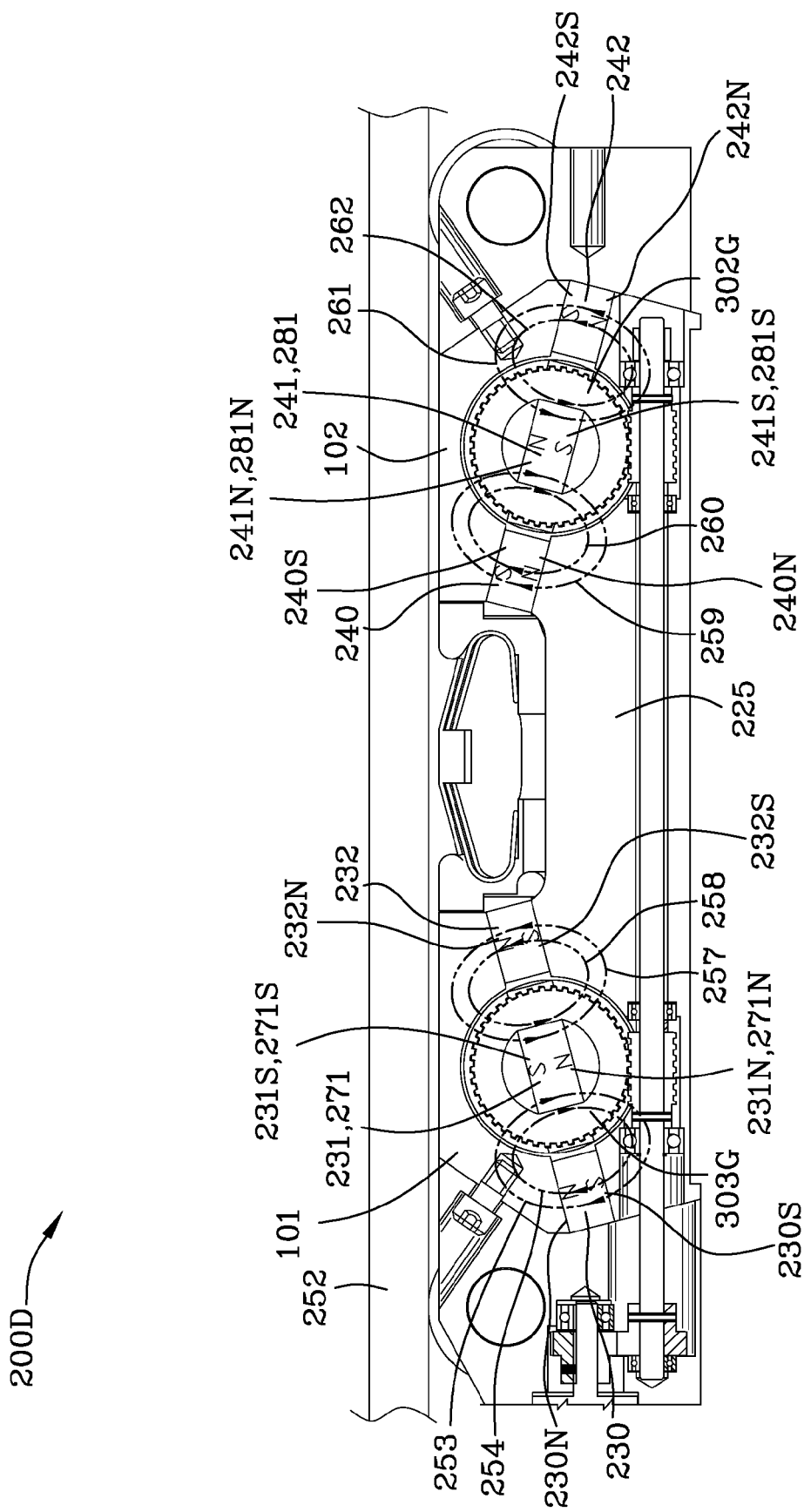
FIG. 2D is a schematic cross-sectional view of the conduit sensor device which includes the magnetic shunt device similar to FIG. 2A with the rotatable shunting magnet rotated 180° from their initial, home, positions with magnetic field lines illustrated.
Figure 2E:
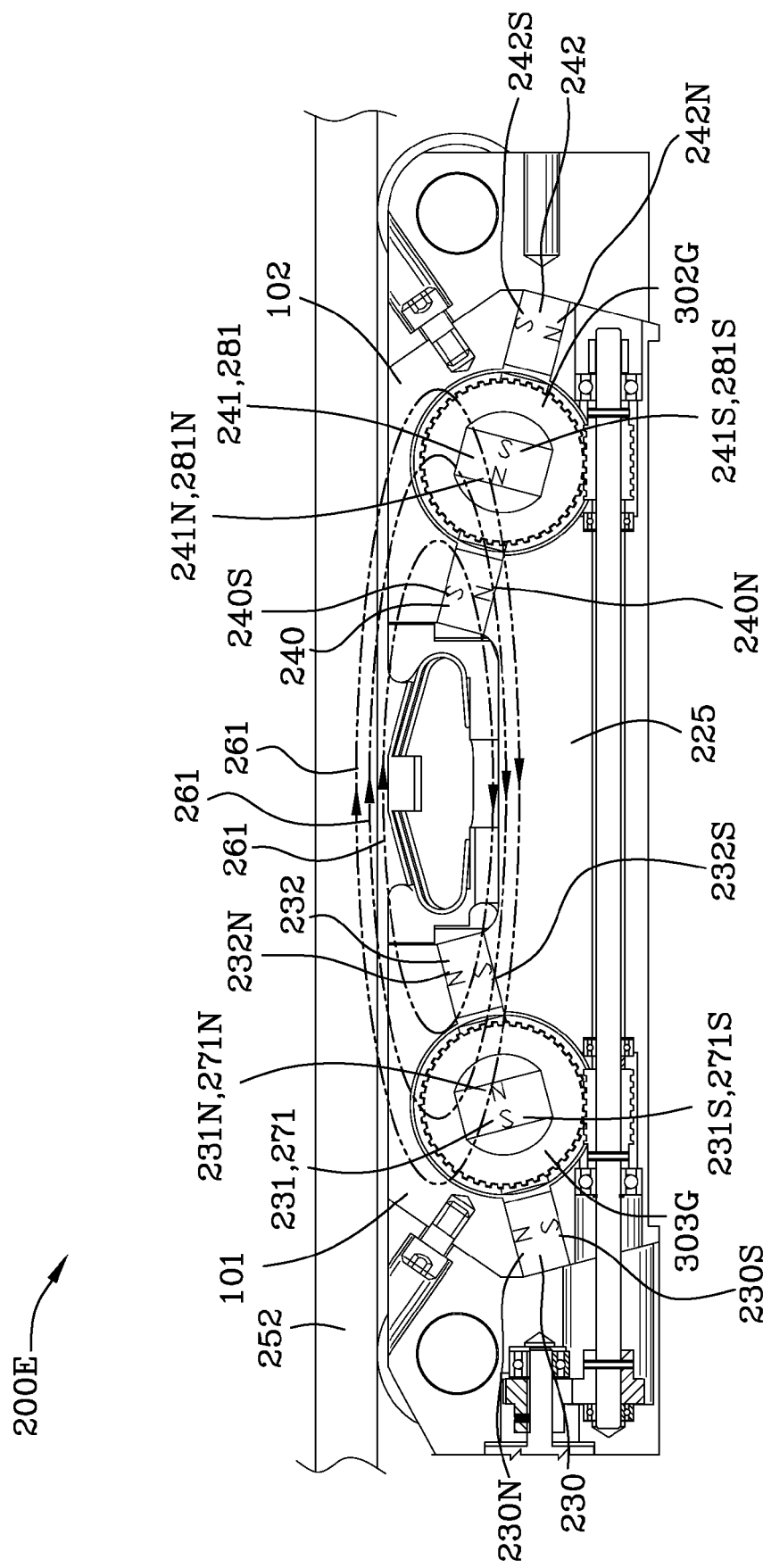
FIG. 2E is a schematic cross-sectional view of the conduit sensor device which includes the magnetic shunt device similar to FIG. 2B with the rotatable shunting magnet rotated 90° from their initial, home, positions with magnetic field lines illustrated.
Figure 2F:
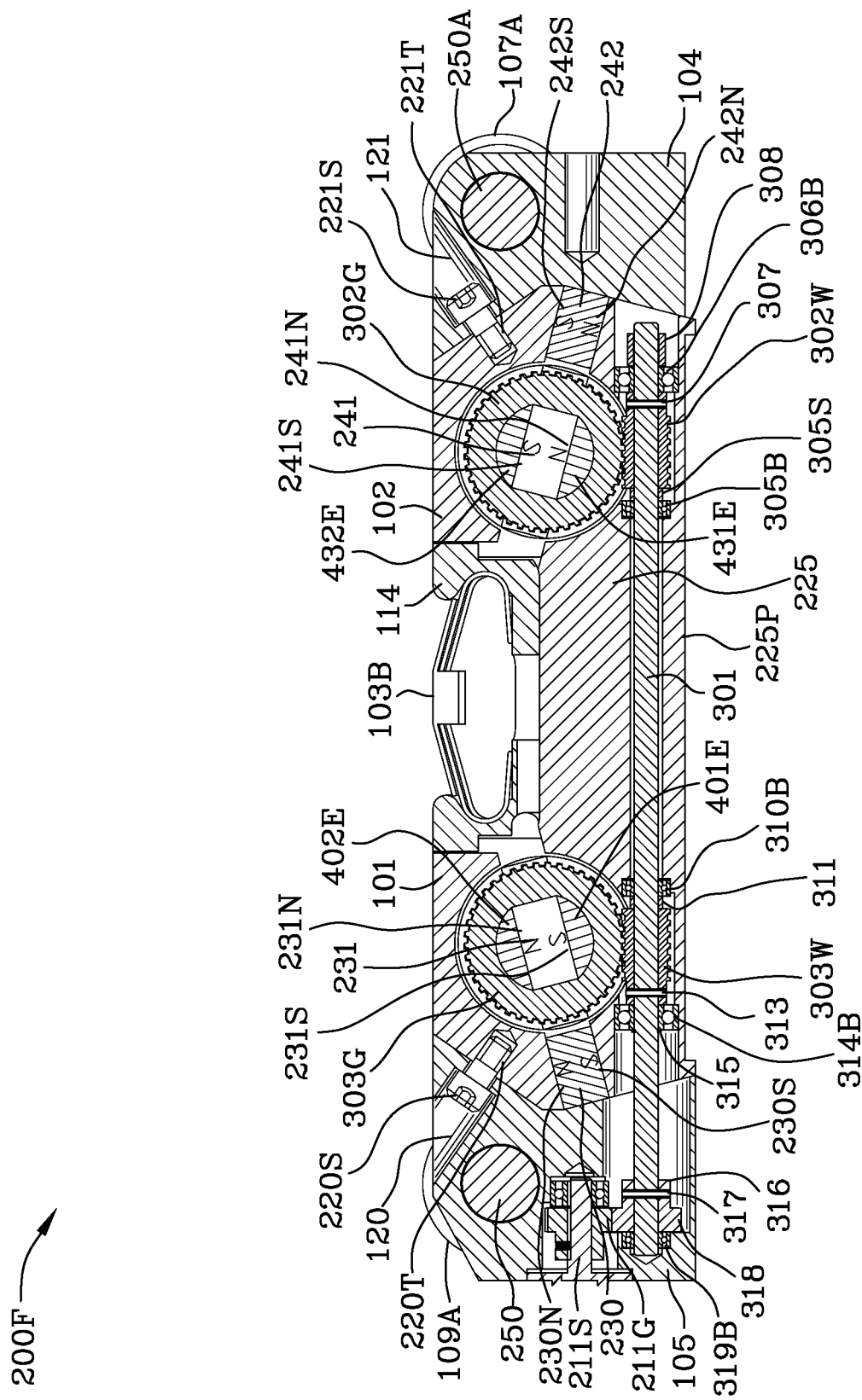
FIG. 2F is a cross-sectional view of another example of the invention wherein one aft permanent magnet is in proximity with the aft rotor shunt/rotatable magnets and wherein one forward permanent magnet is in proximity with forward rotor shunt/rotatable magnets.

Referring to FIGS. 2-2F, an unnumbered air gap exists between the aft shunt rotor/rotatable magnets 231, 271 and backing bar 225, permanent magnets 230, 232, and pole 101. Similarly, an unnumbered air gap exists between the forward shunt rotor/rotatable magnets 241, 281 and backing bar 225, permanent magnets 240, 242 and pole 102. The air gaps are between 0.015 to 0.20 inches. It is highly desirable to minimize the air gaps to enhance the magnetic circuit when desired as set forth in the drawings.

FIG. 4 is a perspective view 400 of the aft rotor shunt illustrating the aft rotatable magnet halves 231, 271, aft rotor gear 303G, male magnet backers 401M, 402M, female magnet backers 401F, 402F, and trunions 460, 471. Guiding protrusion 461 extends from trunion 460 and functions as a guide within slots formed in side wall 110 as described in detail hereinafter in connection with FIG. 6A. FIG. 4J illustrates trunion 471, shaft 462O, and protrusion 461A. Protrusion 461A interengages a slot in side wall 113 which is described in more detail hereinafter. Shaft 462S extends from trunion 460. Screw 464 is threaded into receptacle 464R of male magnet backer 401M and through female magnet backer 402F. Screw 474 is threaded into a corresponding receptacle 402M. and through female magnet backer 401F. Male extensions 401E, 402E extend over and below aft rotatable magnets 231, 271 when the aft rotor shunt is assembled as illustrated in FIGS. 4 and 4D. Male extensions 401E, 402E include arc-shaped surfaces which interfit interior arc-shaped surfaces 415, 416 of rotor gear 303G and arc shaped cavities 410, 411 in female magnet backers 401F, 402F as illustrated in FIGS. 4A and 4C.

FIG. 4A is an exploded perspective view 400A of the aft rotor shunt illustrating the aft rotatable magnet halves 231, 271. Aft rotatable magnet half 231 includes a north pole 231N and a south pole 231S. Aft rotatable magnet half 271 includes a north pole 271N and a south pole 271S.

FIG. 4B is a front view 400B of the aft rotor gear 303G illustrating worm gear teeth (unnumbered) along with inner flat surfaces 413, 414, and arc-shaped surfaces 415, 416. FIG. 4C is a perspective view 400C of one set of male 401M and female 402F magnet backers of the aft rotor shunt.

FIG. 4D is a cross-sectional view 400D taken along the lines 4B-4B of FIG. 1C and illustrates the aft rotatable rotor shunt and the aft rotatable magnet halves 231, 271. Shafts 462S, 462O are illustrated residing within bearings 491, 492, respectively. Side keeper plate 110 includes a recess 460R housing bearing 491 and side keeper plate 113 includes a recess housing bearing 492. Trunion 460 interengages male magnet backer 402M and female magnet backer 402F. Screws 464, 474 viewed in FIG. 4A are not illustrated in the cross-sectional view of FIG. 4D. Screws 464, 474 are used to fasten male halves 401M, 402M to the opposite trunion. Additionally, adhesive 495, 495A, 495B, 495C, 495D is used to secure the magnet backers and rotatable magnets together.

Still referring to FIGS. 2 and 4D, male extension 402E of male magnet backer 402M along with female magnet backer 401F secures rotatable magnet half 231 from above while male magnet backer 401M secures rotatable magnet half 231 from below. Similarly, male magnet backer 402M secures rotatable magnet half 271 from above. Male extension 401E of male magnet backer 401M along with female magnet backer 402F secures rotatable magnet half 271 from below.

Still referring to FIG. 4D, helical gear 303W is depicted diagrammatically as meshing with rotor gear 303G. These gear sets are sometimes referred to as worm-worm gear. Rotor gear 303G is driven by helical gear 303W. Rotatable magnet halves 231, 271 function as a single magnet and are rotated with rotor gear 303G. The entire rotor shunt rotates in unison with rotor gear 303G.

Figure 4H:
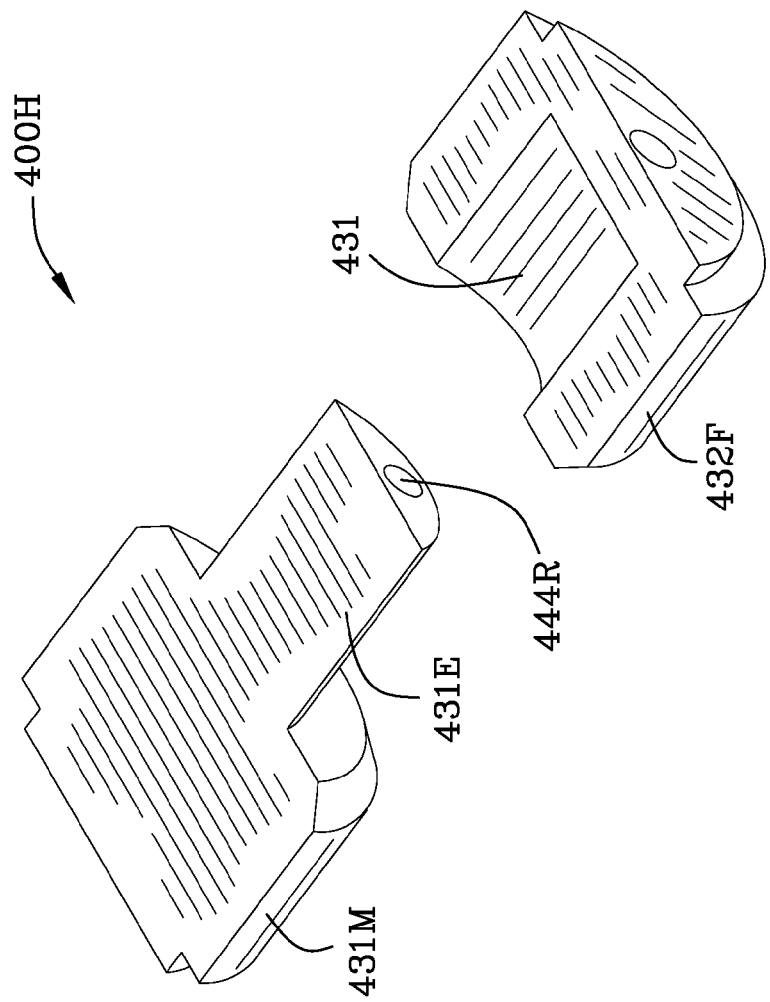
FIG. 4H is a perspective view of one set of the male and female rotor backs of the forward rotor shunt.
Figure 4G:
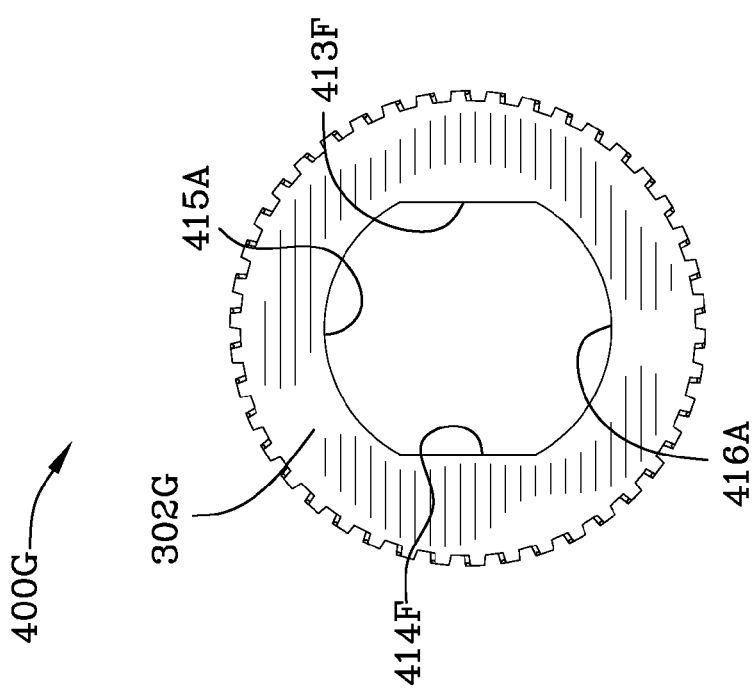
FIG. 4G is a front view of the forward rotor.
Figure 4I:
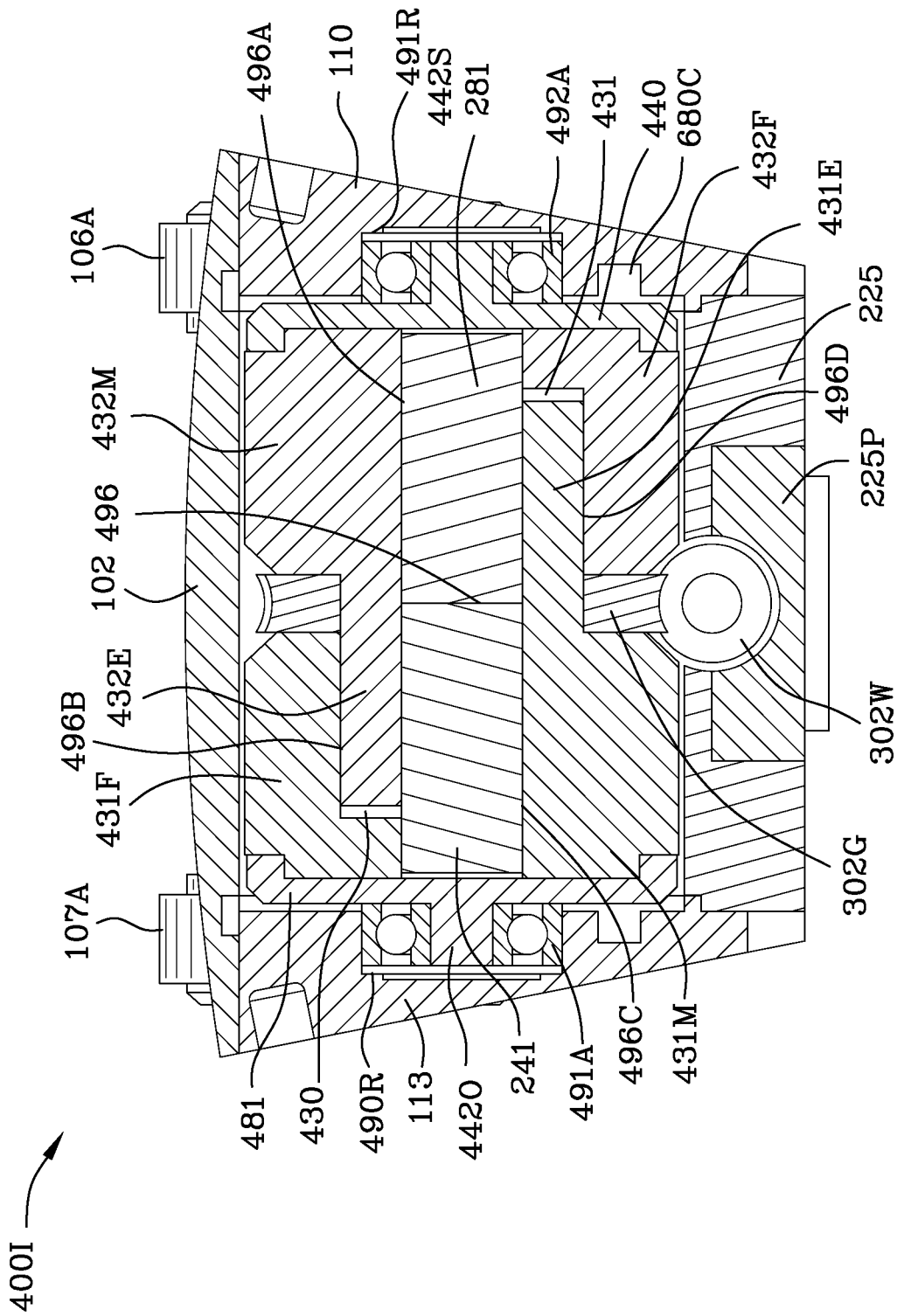
FIG. 4I is a cross-sectional view taken along the lines 4I-4I of FIG. 1C.

FIG. 4E is a perspective view 400E of the forward rotor shunt. FIG. 4F is an exploded perspective view 400F of the forward rotor shunt. FIG. 4G is a front view 400G of the forward rotor 302G. FIG. 4H is a perspective view 400H of the male 431M and female 432F magnet backers of the forward rotor shunt. FIG. 4I is a cross-sectional view 400I taken along the lines 4I-4I of FIG. 1C. The structure of the forward rotor shunt is the same as the aft rotor shunt.

Figure 4K:
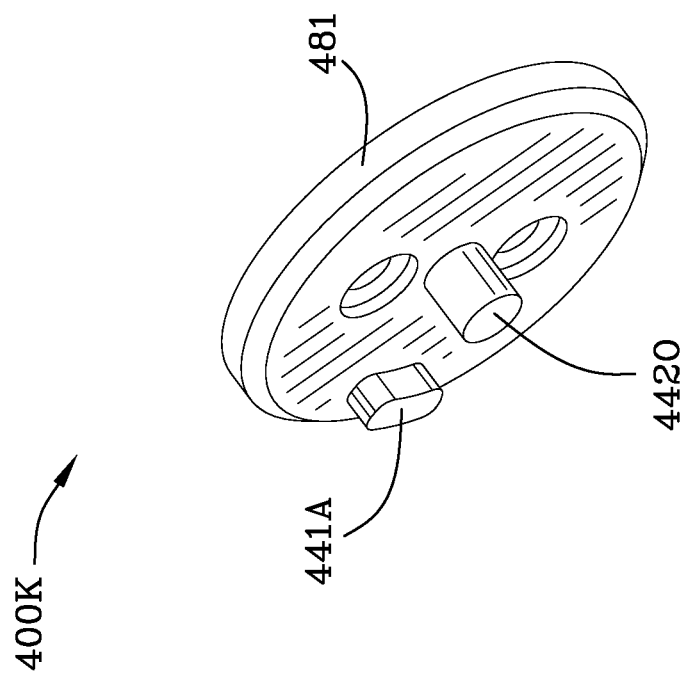
FIG. 4K is a view of a trunion of the forward rotor shunt.
Figure 4J:
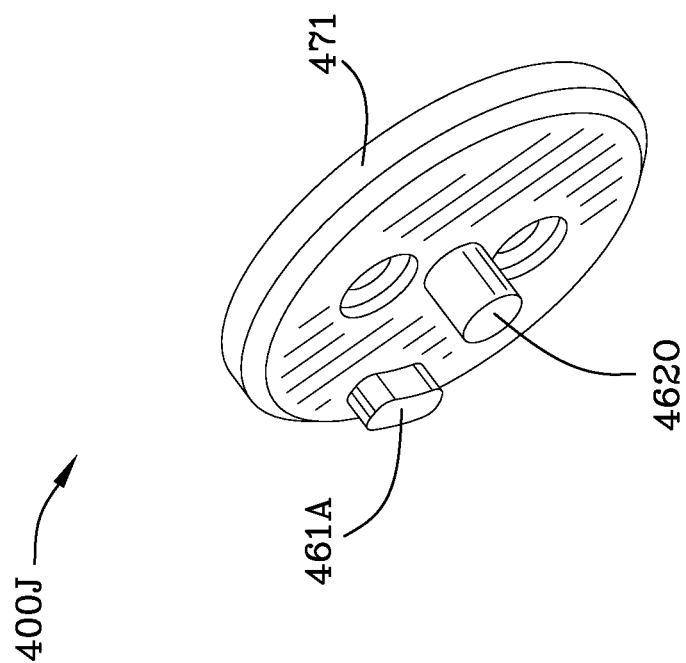
FIG. 4J is a view of a trunion of the aft rotor shunt.

FIG. 4E is a perspective view 400E of the forward rotor shunt illustrating the forward rotatable magnet halves 241, 281, forward rotor gear 302G, male magnet backers 431M, 432M, female magnet backers 431F, 432F and trunions 440, 481. Guiding protrusion 441 extends from trunion 440 and functions as a guide within a slot formed in side wall 110 as described in detail hereinafter. FIG. 4K illustrates trunion 481, shaft 442O, and protrusion 441A. Protrusion 441A interengages a slot in side wall 113. Shaft 462S extends from trunion 440. Screw 444 is threaded into receptacle 444R of male magnet backer 431M and through female magnet backer 432F. Screw 484 is threaded into a corresponding receptacle male magnet backer 432M and through male magnet backer 432M and through female magnet backer 431F. Male extensions 432E, 431E extend over and below forward rotatable magnets 241, 281 when the forward rotor shunt is assembled as illustrated in FIGS. 4E and 4I. Male extensions 431E, 432E include arc-shaped surfaces which interfit interior arc-shaped surfaces 415A, 416A of rotor gear 302G and arc shaped cavities 430, 431 as illustrated in FIGS. 4F and 4H.

FIG. 4F is an exploded perspective view 400F of the forward rotor shunt illustrating the forward rotatable magnet halves 241, 281. Forward rotatable magnet half 241 includes a north pole 241N and a south pole 241S. Forward rotatable magnet half 281 includes a north pole 281N and a south pole 281S.

FIG. 4G is a front view 400G of the forward rotor gear 302G illustrating worm gear teeth (unnumbered) along with inner flat surfaces 413F, 414F, and arc-shaped surfaces 415A, 416A. FIG. 4H is a perspective view 400H of one set of male 431M and female 432F magnet backers of the forward rotor shunt. Male extension 431E of male magnet backer 431M interfits cavity 431 of female magnet backer 432F.

FIG. 4I is a cross-sectional view 400I taken along the lines 4I-4I of FIG. 1C and illustrates the forward rotatable rotor shunt and the forward rotatable magnets 241, 281. Shafts 442S, 442O are illustrated residing within bearings 492A, 491A, respectively. Side keeper plate 110 includes a recess 491R housing bearing 492A and side keeper plate 113 includes a recess 490R housing bearing 491A. Trunion 481 interengages male magnet backer 431M and female magnet backer 431F. Screws 444, 484 viewed in FIG. 4F are not illustrated in the cross-sectional view of FIG. 4I. They are used to fasten the male halves 431M, 432M to the opposite trunion. Additionally, adhesive 496, 496A, 496B, 496C, 496D is used to secure the magnet backers and rotatable magnets together to form the forward rotor shunt.

Still referring to FIGS. 2 and 4I, male extension 432E of male magnet backer 432M along with female magnet backer 431F secures rotatable magnet half 241 from above while male magnet backer 431M secures rotatable magnet half 241 from below. Similarly, male magnet backer 432M secures rotatable magnet half 281 from above. Male extension 431E of male magnet backer 401M along with female magnet backer 432F illustrates secures rotatable magnet half 281.

Still referring to FIG. 4I, helical gear 302W is depicted diagrammatically as meshing with rotor gear 302G. As stated above, these gear sets are sometimes referred to as worm-worm gear.

Referring to FIG. 2, shaft support plate 225P supports shunt shaft bearings as indicated previously and also keeps dirt and debris out of the meshing gears, 303W, 303G and 302W, 302G.

Still referring to FIG. 2, pole 101 as illustrated is the north pole of the magnetic shunt sensor device. Pole 102 as illustrated in FIG. 2 is the south pole of the magnetic shunt sensor device. As previously stated, a plurality of magnet shunt sensor devices comprise a pipeline inspection device.

The aft permanent magnets 230, 232 are positioned with their north poles above their south poles. Similarly, the rotatable magnets 231, 271 are positioned with their respective north poles above the south poles. In FIG. 2 the aft magnet set, 230, 232, 231, 271 as shown creates, in sum, a magnetic north pole on the upper incline of the magnet set and a magnetic south pole on the lower inclined of the magnet set. The inclination of the magnet set does not affect the magnet field created by the magnet set.

Figure 6C:
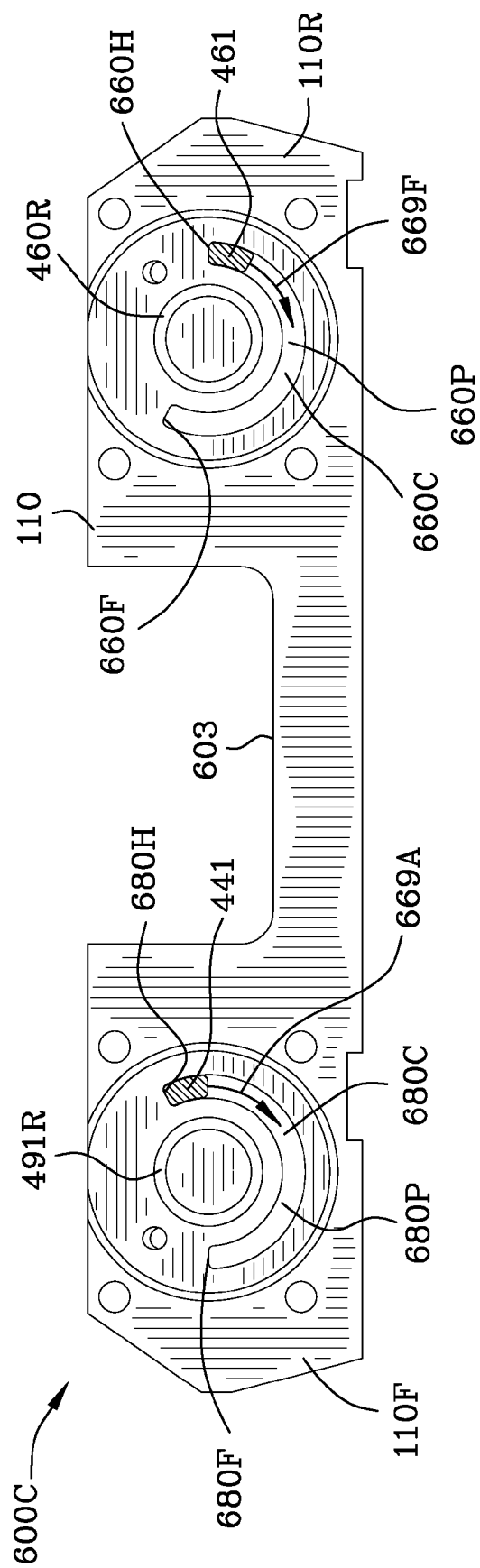
FIG. 6C illustrates the inside of the side keeper block of FIG. 6 similar to FIG. 6A and further illustrates protrusions in the slots of the side keeper.

Still referring to FIG. 2, pole 102 as illustrated is the south pole created by the forward magnet set. The forward magnets 241, 281 are positioned with their south poles above their north poles. The forward permanent magnets 240, 241 are positioned with their south poles above their north poles. In FIG. 2 the forward magnet set, 240, 242, 241, 281 as shown creates, in sum, a magnetic south pole on the upper incline of the magnet set and a magnetic north pole on the lower incline of the magnet set. In the configuration of FIG. 2, the aft rotor shunt and aft rotatable magnets 231, 271 and the forward rotor shunt and forward rotatable magnets are in home position. Referring to FIGS. 6, 6A and 6C, protrusion 461 is shown in home position as indicated by reference numeral 660H. Home position is defined as the position of the rotor shunt and the aft rotatable magnets as illustrated in FIG. 2. The protrusion 461 is aligned with the rotatable magnets. Similarly, protrusion 441 is illustrated in home position in FIG. 6C. Arrows 669F, 669A indicate the direction of rotation of the rotor shunt beginning at the home position as indicated by the position of the protrusion 461 in arcuate slot 660C and the position of the protrusion 441 in arcuate slot 680C.

FIG. 6 illustrates 600 the outside of the side keeper plate (side plate) 110 of the magnetic sensor shunt device. The side plate is affixed to the backing bar with unnumbered threaded connections such as those illustrated in FIG. 1. Reference numeral 603 indicates an opening for the saddle 114. Reference numeral 110F signifies the forward portion of the device and reference numeral 110R signifies the aft or rear portion of the device.

FIG. 6A illustrates 600A the inside of the side keeper 110 of FIG. 6. A first arcuate slot 660C is illustrated generally in the aft or rear portion 110R of the side keeper (side plate) 110. Receptacle 460R houses bearing 491 which supports the shaft of the aft rotor shunt. Receptacle 460R is centrally located with respect to arcuate slot 660C. As illustrated in FIG. 6C, protrusion 461 resides in slot 660C and is guided therein. Slot 660C serves to limit the travel of the protrusion and, hence, the aft rotor shunt. Slot 660C also orients protrusion 461 and aft rotatable magnet halves 231, 271 in their home position during assembly.

Still referring to FIGS. 6A and 6C, home positions 660H, 680H of protrusions 461, 441 are shown, respectively. Arrows 669F, 669A indicates the direction of rotation of the aft rotor shunt and forward rotor shunt, respectively. Home positions 660H, 680H are referred to herein as being at 0° in an arc which ranges from 0° to 180°. Reference numerals 660F, 680F indicate the final position, 180°, from the initial, home position. "Final" as used herein is just a reference position and it does not mean a permanent position as the protrusions may be driven to any one of the positions available between 0° and 180°. Protrusions 461, 442 may move through an angle of 180° between home position 660H and final position 660F.

A second arcuate slot 680C is illustrated generally in the forward portion 110F of the side keeper 110. Receptacle 491R houses bearing 492A which supports the shaft of the forward rotor shunt. Receptacle 491R is centrally with respect to slot 680C. As illustrated in FIG. 6C, protrusion 441 resides in slot 680C and is guided therein. Slot 680C also orients protrusion 441 and the forward rotatable magnet halves 241, 281 in their home position during assembly.

Aft arcuate slot 660C allows protrusion 461 to make a 180° arc. Home position 660H and final position 660F function as stops or limits. Similarly, forward arcuate slot 680C allows protrusion 441 to make a 180° arc. Home position 680H and final position 680F function as stops or limits. Although initially positioned as set forth in FIG. 2, the protrusions 461, 444, and hence the rotor shunts and rotatable magnets, may be driven bidirectionally by shunt shaft 301, helical gears 302W, 303W and rotor gears (worm gears) 302G, 303G to any desired position between 0° (home position) to 180° (final position). The forward and aft helical gears 302W, 303W are driven in the same direction and rotor gears 302G, 303G follow in the same rotational direction. In other words, if shunt shaft 301 is rotated in the clockwise direction (as viewed from the end of shaft 301 supported by bearing 319B), then worm gears 302G, 303G are rotated in the same clockwise direction. Similarly if shunt shaft is driven in a clockwise direction (as viewed from the end of shaft 301 supported by bearing 319B), then worm gears 302G, 303G will be rotated in the counterclockwise direction.

Referring to FIGS. 2, 6A and 6C, aft and forward rotor shunts and rotatable magnets can only be rotated in the clockwise direction as the protrusions are in their home positions. When the aft and forward rotor shunt are rotated to their final positions through an arc of 180°, the rotatable magnets are in the positions illustrated in FIGS. 2A, 2D and the 461, 441 engage stop 660F, 680F as illustrated in FIG. 6C.

FIG. 6B is a cross-sectional view 600B taken along the lines 6B-6B of FIG. 6A illustrating the bearing receptacle 460R and the first arcuate slot (aft slot) in the side plate 110.

Poles 101, 102 and backing bar 225 are ferromagnetic. Backing bar 225 is made of 1008 steel capable of carrying a higher magnetic field than typical 1018 steel. Poles 101, 102 are made of 1018 steel. FIG. 2C is a schematic cross-sectional view 200C of the conduit sensor device which includes the magnetic shunt device similar to FIG. 2 with magnetic field lines 251 illustrated. Each of the permanent and rotatable magnets has a BH product of 45MGOe which equates to 358.1 kJ/m$^3$. The combined surface area of permanent magnets 230 and 232 in the aft rotor shunt is equal to the combined surface area of the aft rotatable magnets 231, 271. Similarly, the combined (total) surface area of permanent magnets 240, 242 of the forward rotor shunt is equal to the combined (total) surface area of the forward rotatable magnets 241, 281. See, FIG. 5D, a diagrammatic view of the aft magnets including the rotatable magnet which illustrates the approximate relative size of the permanent magnets and the rotatable magnets for both the aft and the forward poles.

Referring to FIG. 2C, the home position of the rotatable magnets is illustrated. The home position of the rotatable magnets is also shown in FIG. 2. The pipe wall 252 is illustrated with a thickness and the magnetic field 251 is illustrated passing entirely through the wall of the pipe 252. The rotatable magnets are illustrated and reference numerals 231, 271 indicate the rotatable magnet halves.

Figure 5D:
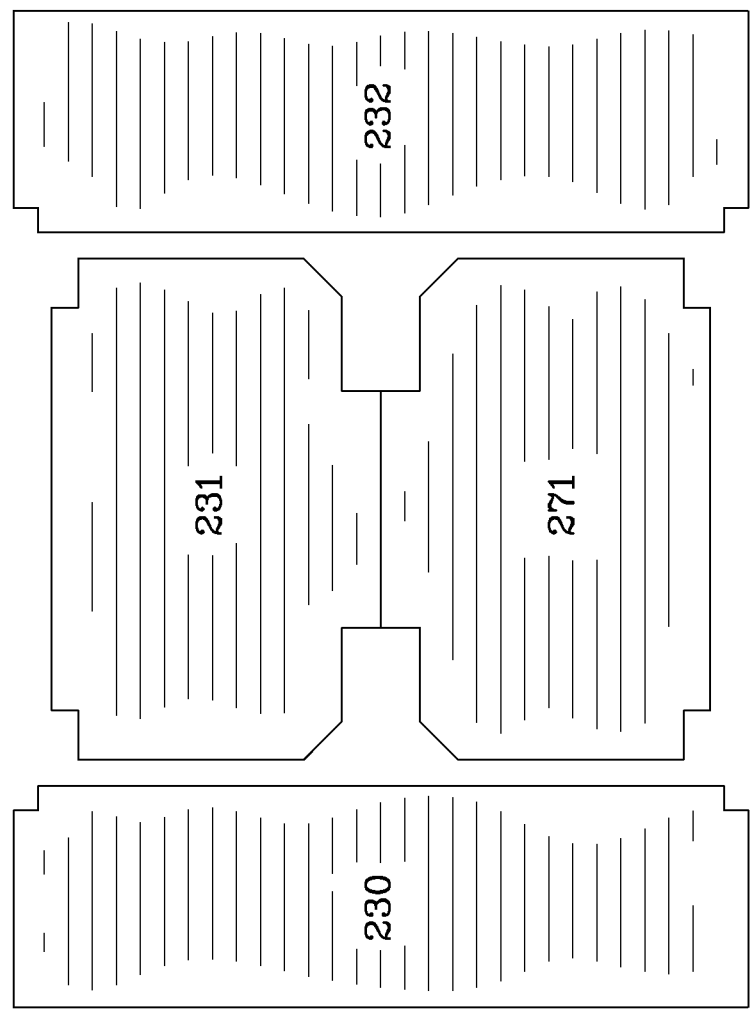
FIG. 5D is a diagrammatic view of the aft magnets including the rotatable magnet.

Referring to FIG. 5D, the thickness of the permanent magnets 230, 232 and the rotatable magnets 231, 271 are equal and the obverse sides of the magnets are equal in area to the viewable sides. The surface area of permanent magnets 230, 232 equal the surface area of the rotatable magnets 231, 271. The invention is not limited to any particular size permanent or rotatable magnets size.

FIG. 2A is a cross-sectional view of the conduit sensor device which includes the magnetic shunt device taken along the lines 2-2 of FIG. 1B with the rotatable shunting magnets rotated 180° from their initial positions to their final positions. Home positions of the rotatable magnets are the same as the home position of the protrusions associated with rotatable magnets. The rotor shunts and the rotatable magnets carried therewith are synchronously driven by the shunt shaft 301 as dictated by the stepper motor. FIG. 2D is a schematic cross-sectional view 200D of the conduit sensor device which includes a magnetic sensor shunt device similar to FIG. 2A with the rotatable shunting magnets 231, 271 and 241, 281 rotated 180° from their initial, home, positions with magnetic field lines illustrated. In this orientation a substantially complete cancellation of the magnetic field is achieved and the magnetic field does not extend into pipe 252. Magnetic field lines are indicated with reference numerals 253, 254, 257, 258 in regard to the aft pole 101 and the magnetic field lines are indicated with reference numerals 259, 260, 261, 262 in regard to the forward pole 102. With the rotatable magnets 231, 271 rotated to final position 660F as illustrated in FIGS. 2A, 2D, and 6A the net magnetic field of the aft pole 101 (aft magnet set 230, 232, 231, 271) has been cancelled. With the rotatable magnets 241, 281 rotated to final position 680F as illustrated in FIGS. 2A, 2D, and 6A the net magnetic field of the forward pole 102 (forward magnet set 240, 241, 281, 242) has been cancelled. Further, the net magnetic field between the poles 101 and 102 has been substantially cancelled. The cancellation of the magnetic field enables the conduit sensor device to pass through the pipeline/conduit and obstructions like a vale or elbow.

FIG. 2B is a cross-sectional view 200B of the conduit sensor device which includes the magnetic shunt device taken along the lines 2-2 of FIG. 1B with the rotatable shunting magnets rotated (231, 271 and 241, 281) 90° from their initial positions. FIG. 2E is a schematic cross-sectional view 200E of the conduit sensor device which includes the magnetic shunt device similar to FIG. 2B with the rotatable shunting magnets 231, 271 and 241, 281 rotated 90° from their initial, home, positions with magnetic field lines illustrated by reference numeral 261. As illustrated in FIG. 2E, the magnetic field lines 261 extend only partially into the conduit/pipeline wall 252. Under certain circumstance, due to pipe wall thickness or the material of the pipe, or the diameter of the pipe, it may be desired to impart some, but not all, of the magnetic field into the conduit pipe. As indicated above, this may be necessary to compensate for the data being taken, and or to compare current data to previously measured data for a given particular pipeline/conduit.

FIG. 2F is a cross-sectional view 200F of another example of the invention wherein one permanent magnet 230 is in proximity with rotatable magnets 231, 271 and wherein one permanent magnet 242 is in proximity with rotatable magnets 241, 281. The rotor shunts/rotatable magnets used in the example of FIG. 2F are driven as previously described herein and have the same structure as previously described herein. Similarly, the drive structure, namely, the shunt shaft and gears, used in the example of FIG. 2F is as previously described herein in connection with the example of FIGS. 2-2E and, as such, is not repeated herein.

FIG. 3 is a top view 300 of the shunt shaft illustrating the aft 303W and forward 302W worms (helical gears) mounted on shunt shaft 301. Both worm gears rotate in the same direction and are of the same orientation. FIGS. 3 and 3A provide larger and better views of the shunt shaft described above in connection with FIG. 2. FIG. 3A is a cross-sectional view 300A taken along the lines 3A-3A of FIG. 3 and provides a larger and better view of the shunt shaft as described above in connection with FIG. 2.

FIG. 5 is a top view 500 of the backing bar 225 and fixed permanent magnets 230, 232, 240, and 242. FIG. 5A is a side view 500A of the backing bar and fixed permanent magnets. Seat 503 for saddle 114 is illustrated. Aft semi-cylindrically shaped opening 501 and forward semi-cylindrically shaped opening 502 in backing bar 225 are illustrated in FIG. 5A. The aft and forward rotor shunts illustrated in FIGS. 4 and 4E are generally cylindrical in nature. Side keeper plates 110 and 113 as illustrated in FIGS. 6, 6A, 6B and 6C support the rotor shunts and position them within the semi-cylindrical openings 501, 502, respectively. The aft and forward rotor shuns are supported in the bearings and are spaced apart from the semi-cylindrically shaped openings 501, 502. The aft and forward rotatable shunts do not engage the backing bar 225 or poles 101, 102, Still referring to FIG. 5, openings 504, 505 in the backing bar accommodate the placement of rotor gears 303G, 302G partially therein, respectively, for meshing engagement with helical gears 303W, 303G mounted on shunt shaft 301. FIG. 5B is a bottom view 500B of the backing bar illustrating cavities 510, 510A which allow needed space for the helical gears 303W, 303G and effectively keep the size of the device to a minimum. Shunt shaft 301 resides in channel 520C. See FIG. 5C, a cross-sectional view taken along the lines 5C-5C of FIG. 5. Channel 520C in the backing bar 225 allows room for shunt shaft 301 to reside therein.

FIG. 7 is a side view 700 of the aft pole 101. Aft pole 101 has the same structure as forward pole 102. FIG. 7A is an end view 700A of the aft pole. FIG. 7B is a rear view 700B of the aft pole 101. FIG. 7C is a bottom view 700C of the aft pole. Reference numeral 701 indicates a semi-circular opening in aft pole 101 which accommodates the curvature of the aft rotor shunt which is generally cylindrically shaped. Surface 702 of pole 101 interengages first aft permanent magnet 230 of aft magnet set and surface 703 interengages second aft permanent magnet 232 of aft magnet set. Rear surface of aft pole 101 includes screw hole 706. Screw 220S viewed in FIG. 2 threadedly 220T interconnects with screw hole 706.

FIG. 8 is an end view 800 of the forward end block. FIG. 8A is perspective view 800A of the forward end block 104.

FIG. 9 is an end view 900 of the aft end block 105 taken along the lines 9-9 of FIG. 1D.

FIG. 9A is a perspective end view 900A of the forward end block 105 illustrating bolt holes 105 for interconnection to stepper motor 11. Reference numeral 105F indicates the flat mating surface of the end block 105.

A process for modifying a magnetic field generated between magnetic poles with the magnetic field 251, 251 in proximity to a ferromagnetic conduit 252 is disclosed and claimed. The process includes the steps of: driving, bidirectionally, a shunt shaft 301 having first 303W and second 302W helical gears; rotating, using the first helical gear and a first rotor gear 303G, a first rotor shunt residing intermediate a first set of permanent magnets 230, 232 forming a first magnetic pole 101, the first rotor shunt includes a first rotatable magnet 231, 271 rotating therewith; synchronously rotating, using the second helical gear 302W and a second rotor gear 302G, a second rotor shunt residing intermediate a second set of permanent magnets 240, 242 forming a second magnetic pole 102, the second rotor shunt includes a second rotatable magnet 241, 281 rotating therewith;

discontinuing the rotation of the first rotor shunt and the second rotor shunt synchronously positioning the first rotatable magnet 231, 271 intermediate the first set of permanent magnets 230, 232 and the second rotatable magnet 241, 281 intermediate the second set of permanent magnets 240, 242; and, modifying the magnetic field 261, 261 generated between the magnet poles. The steps of: rotating, using the first helical gear and a first rotor gear, a first rotor shunt residing intermediate a first set of permanent magnets forming a first magnetic pole, the first rotor shunt includes a first rotatable magnet rotating therewith, and, synchronously rotating, using the second helical gear and a second rotor gear, a second rotor shunt residing intermediate a second set of permanent magnets forming a second magnetic pole, the second rotor shunt includes a second rotatable magnet rotating therewith, include rotating the first and second shunt rotors between 0°, home position, and 180°, final position, the first and second rotatable magnets rotating therewith, respectively.

The process may be performed with a first rotor shunt which includes a protrusion 461 extending therefrom and second rotor shunt which includes a protrusion 441 extending therefrom. The process includes the further step of: guiding and interengaging the protrusion 461 of the first rotor shunt in a first arcuate slot 660C in a side wall 110. The first arcuate slot 660C extending between 0°, home position, and 180°, final position. The process further includes the step of guiding and interengaging the protrusion 441 of the second rotor shunt in a second slot 680C in side wall 110. The second arcuate slot 680C extending between 0°, home position, and 180°, final position.

One of the features of the process for modifying a magnetic field generated between magnetic poles, 101, 102 includes cancelling the magnetic field when the rotation of the protrusions of the first and second rotor shunts are positioned in the first and second slots at 180°. See FIGS. 2A and 2C.

Another example of the conduit sensor device comprises first and second pairs of permanent magnets. The first pair of permanent magnets includes a first magnet and a second magnet. The first and second magnets include outer surfaces, the outer surfaces of the first magnet have a first area and the outer surfaces of the second magnet have a second area. A second pair of permanent magnets. The second pair of permanent magnets includes a fifth magnet and a sixth magnet and the fifth and the sixth magnets include outer surfaces.

The outer surfaces of the fifth magnet have a fifth area and the outer surfaces of the sixth magnet have a sixth area. A first rotor shunt is interposed between the first pair of permanent magnets and a second rotor shunt is interposed between the second pair of permanent magnets. A shunt shaft runs the length of the device and includes a first helical worm gear and a second helical worm gear mounted thereon. The first rotor shunt includes a first rotatable magnet and a first rotor gear and the first rotatable magnet and the first rotor gear are locked together such that the first rotatable magnet rotates with the first rotor gear. The first helical worm gear meshes with the first rotor gear and drives the first rotor gear and the first rotatable magnet. The second rotor shunt includes a second rotatable magnet and a second rotor gear. The second rotatable magnet and the second rotor gear are locked together such that the second rotatable magnet rotates with the second rotor gear. The second helical worm gear meshes with the second rotor gear and drives the second rotor gear and the second rotatable magnet. The first rotatable magnet is comprised of a third and fourth magnet. The third and fourth rotatable magnets include outer surfaces, the outer surface of the third magnet has a third area and the outer surface of the fourth magnet includes a fourth area. The second rotatable magnet is comprised of a seventh and eighth magnet. The seventh and eighth magnets include outer surfaces. The outer surface of the seventh magnet has a seventh area and the outer surface of the eight magnet includes an eighth area. The area of the first magnet and the area of the second magnet, when combined, equal the combined area of the third and fourth magnets. The area of the fifth magnet and the area of the sixth magnet, when combined, equal the combined area of the fifth and sixth magnets. The first rotatable magnet and the second rotatable magnet are synchronously rotated and positioned.

REFERENCE NUMERALS

100—perspective view of the conduit sensor device which includes the magnetic shunt device
100A—another perspective view of the conduit sensor device which includes the magnetic shunt device
100B—top view of the conduit sensor device which includes the magnetic shunt device
100C—side view of the conduit sensor device which includes the magnetic shunt device
100D—perspective view of the conduit sensor device which includes the magnetic shunt device without the drive motor
101—aft pole
102—forward pole
103, 103A, 103B, 103C, 103D, 103E—sensors
104—forward end block
105—aft (rear) end block
105A—wire groove in end block 105
105B—bolt hole
105F—flat face of end block
106, 107, 108, 109—wheels
106A, 107A, 108A, 109A—rubber grips or tires
110—side plate
110A—wire groove in side plate 110
110E—forward portion of side plate 110
110R—rearward (aft) portion of side plate 110
111—stepper motor
112—controls for stepper motor
113—side plate
113A—wire groove in aft end block
113B—wire groove in side plate 113
113F—forward end
113R—rearward (aft) end
114—saddle
120—bolt hole for attaching aft end block 105 to backing bar 225
121—bolt hole for attaching forward end block 104 to backing bar 225
177A, 178A—support arm
200—cross-sectional view of the conduit sensor device which includes the magnetic shunt device taken along the lines 2-2 of FIG. 1B
200A—cross-sectional view of the conduit sensor device which includes the magnetic shunt device taken along the lines 2-2 of FIG. 1B with the rotatable shunting magnet rotated 180° from its initial position
200B—cross-sectional view of the conduit sensor device which includes the magnetic shunt device taken along the lines 2-2 of FIG. 1B with the rotatable shunting magnet rotated 90° from its initial position 200C—a cross-sectional view of the conduit sensor device which includes the magnetic shunt device similar to FIG. 2 with magnetic field lines illustrated
200D—cross-sectional view of the conduit sensor device which includes the magnetic shunt device similar to FIG. 2A with magnetic field lines illustrated
200E—cross-sectional view of the conduit sensor device which includes the magnetic shunt device similar to FIG. 2B
200E—cross-sectional view of another example of the invention wherein one permanent magnet 230 is in proximity with rotatable magnets 231, 271 and wherein one permanent magnet 242 is in proximity with rotatable magnets 241, 281.
211G—input gear driven by stepper motor
211S—wheel shaft
220S—screw in hole 120 mating with backing bar 225
220T—threaded connection
221S—screw in hole 121 mating with backing bar 225
221T—threaded connection
225—backing bar
225P—shaft support plate
230—first aft permanent magnet of aft magnet set
230N—north of first aft permanent magnet of aft magnet set
230S—south of first aft permanent magnet of aft magnet set
231—rotatable magnet of aft magnet set
231N—north of rotatable magnet of aft magnet set
231S—south of rotatable magnet of aft magnet set
232—second aft permanent magnet of aft magnet set
232N—north of second aft permanent magnet of aft magnet set
232S—south of second aft permanent magnet of aft magnet set
240—second permanent magnet of forward magnet set
240N—north of second permanent magnet of forward magnet set
240S—south of second permanent magnet of forward magnet set
241—rotatable magnet of aft magnet set
241N—north of rotatable magnet of forward magnet set
241S—south of rotatable magnet of forward magnet set
242—first permanent magnet of forward magnet set
242N—north of first permanent magnet of forward magnet set
242S—south of first permanent magnet of forward magnet set
250, 250A—wheel shaft
251—field lines
252—pipe wall
253, 254—field lines
257, 258—field lines
259, 260—field lines
261, 262—field lines
271—rotatable magnet of aft magnet set
271N—north of rotatable magnet of aft magnet set
271S—south of rotatable magnet of aft magnet set
281—rotatable magnet of aft magnet set
281N—north of rotatable magnet of aft magnet set
281S—south of rotatable magnet of aft magnet set
300—top view of the shunt shaft illustrating the forward and aft worms
300A—cross-sectional view taken along the lines 3A-3A of FIG. 3
301—shunt shaft
302G—forward worm gear
302W—forward worm
303G—aft worm gear
303W—aft worm
305B—bearing for forward worm-worm gear set
305S—spacer
306B—bearing for forward worm-worm gear set
307—pin
308—shaft spacer
310B—bearing for aft worm-worm-gear set
311—spacer
313—pin
314B—bearing for aft worm-worm-gear set
315—snap-ring
316—gear
317—pin
318—gear teeth
319B—bearing adjacent and supporting shunt shaft 301
400—perspective view of the aft rotor shunt
400A—exploded perspective view of the aft rotor shunt
400B—front view of the aft rotor
400C—perspective view of one set of male and female rotor backs
400D—cross-sectional view taken along the lines 4B-4B of FIG. 1C
400E—perspective view of the forward rotor shunt
400E—exploded perspective view of the forward rotor shunt
400G—front view of the forward rotor
400H—perspective view of one set of the male and female rotor backs
400I—cross-sectional view taken along the lines 4I-4I of FIG. 1C
401E—male extension of male magnet backer 401M
401F—female magnet backer
401M—male magnet backer
402E—male extension of male magnet backer 402M
402F—female magnet backer
402M—male magnet backer
410—arc-shaped cavity in female magnet backer 401F
411—arc-shaped cavity in female magnet baker 402F
413, 414—flat inner surface of worm gear for restraining magnet movement
413F, 414F—flat inner surface of worm gear for restraining magnet movement
415, 415—arc-shaped inner surface of worm gear
415A, 416A—arc-shaped inner surface of worm gear
430—cavity in female magnet backer 431F
431—cavity in female magnet backer 402F
431E—male extension of male magnet backer 431M
431F—female magnet backer
431M—male magnet backer
432E—male extension of male magnet backer 432M
432F—female magnet backer
432M—male magnet backer
440—trunion mating with female magnet backer 431F and male backer 431M
441, 441A—protrusion
442O—shaft on trunion 481
442S—shaft on trunion 441
443, 444—screws
444—receptacle
460—trunion mating with male magnet backer 402M and female magnet backer 402F
460R—receiving cylinder for bearing of shunt rotor
461, 461A—protrusion
462—trunion/rotor shunt shaft
462O—shaft extending from trunion 471
463, 464—screws
464R—receptacle for screw 464

471—trunion mating with male magnet backer 401M and female magnet backer 401F
471R—receiving cylinder for bearing of shunt rotor in side wall 113
473, 474—screws
480R—receiving cylinder for bearing of shunt rotor
481—trunion mate with male magnet backer 432M and female magnet backer 432F
483, 484—screws
490R—receptacle for receiving bearing 491A
491R—receptacle for receiving bearing 492A
491, 492—bearings
491A, 492A—bearings
495, 495A, 495B, 495C, 495D—adhesive
496, 496A, 496B, 496C, 496D—adhesive
500—top view of the backing bar and fixed permanent magnets
500A—side view of the backing bar and fixed permanent magnets
500B—bottom view of the backing bar
500C—cross-section view of the backing bar and fixed permanent magnets taken along the lines 5C-5C of the backing bar
500D—diagrammatic representation of the magnet layout of the aft rotor shunt
501—aft semi-cylindrical opening in backing bar 225
502—forward semi-cylindrical opening in backing bar 225
503—saddle seat
504—aft opening in backing bar 225 for worm-worm gear engagement
505—forward opening in backing bar 225 for worm-worm gear engagement
510, 510A—cavity in backing bar 225 housing shaft helical worm
520—channel in backing bar for shunt shaft
600—outside of the side keeper block of one side of the magnetic sensor shunt device
600A—inside of the side keeper block of FIG. 6
600B—cross-sectional view taken along the lines 6B-6B of FIG. 6A
660C—channel for aft rotor shunt in inner portion of side wall 110
660H—home position of protrusion
660E—final stop of protrusion
660—home position of protrusion
660P—intermediate position of protrusion
680C—channel for aft rotor shunt in inner portion of side wall 110
680E—final stop for protrusion
680H—home position
680P—intermediate position of protrusion
700—side view of the aft pole
700A—an end view of the aft pole
700B—perspective view of the aft pole
700C—bottom view of the aft pole
701—semi-circular opening in aft pole
702—surface interengaging first aft permanent magnet 230 of aft magnet set
703—surface interengaging second aft permanent magnet 232 of aft magnet set
704—rear surface of aft pole
706—screw hole
800—end view of forward end block
800A—perspective view of the forward end block
801—front surface of forward end block
900—end view of the aft end block taken along the lines 9-9 of FIG. 1D
900A—end view of the aft end block taken along the lines 9-9 of FIG. 1D
901—bolt hole opening The invention has set forth by way of example only and those skilled in the art will readily recognize that changes may be made to the invention without departing from the spirit and the scope of the appended claims.

The invention claimed is:

1. A conduit sensor device, comprising:
an aft pole, said aft pole includes an aft magnet set, said aft magnet set includes a first aft permanent magnet, a second aft permanent magnet, and a first rotatable magnet interposed between said first aft permanent magnet and said second aft permanent magnet;
and, a sensor.

2. A conduit sensor device, comprising:
a forward pole, said forward pole includes a forward magnet set, said forward magnet set includes a first forward permanent magnet, a second permanent magnet, and a second rotatable magnet interposed between said first forward permanent magnet and said second permanent magnet;
and, a sensor.

3. A conduit sensor device as claimed in claim 1, further comprising:
a backing bar supporting said first aft permanent magnet and said second permanent magnet; and,
means for securing said first aft permanent magnet and said second permanent magnet to said backing bar.

4. A conduit sensor device as claimed in claim 2, further comprising:
a backing bar supporting said first forward permanent magnet and said second permanent magnet; and,
means for securing said first forward permanent magnet and said second permanent magnet to said backing bar.

5. A process for modifying a magnetic field generated between magnetic poles, said magnetic field in proximity to a ferromagnetic conduit, a device for modifying said magnetic field, said device includes: an aft pole, said aft pole includes an aft magnet set, said aft magnet set includes a first aft permanent magnet, a second aft permanent magnet, and a first rotatable magnet interposed between said first aft permanent magnet and said second aft permanent magnet; a forward pole, said forward pole includes a forward magnet set, said forward magnet set includes a first forward permanent magnet, a second permanent magnet, and a second rotatable magnet interposed between said first forward permanent magnet and said second permanent magnet; a backing bar supporting said first aft permanent magnet and said second permanent magnet; and, means for securing said first aft permanent magnet and said second permanent magnet to said backing bar; a backing bar supporting said first forward permanent magnet and said second permanent magnet; means for securing said first forward permanent magnet and said second permanent magnet to said backing bar; and, a sensor, comprising the steps of:
driving, a shunt shaft having first and second helical gears;
rotating said first rotatable magnet;
synchronously rotating said second rotatable magnet;
discontinuing the rotation of said first rotatable magnet and said second rotatable magnet; and,
modifying said magnetic field generated between said magnet poles.

* * * * *

UNITED STATES PATENT AND TRADEMARK OFFICE
CERTIFICATE OF CORRECTION

PATENT NO. : 9,625,419 B2  
APPLICATION NO. : 13/561924  
DATED : April 18, 2017  
INVENTOR(S) : Laursen et al.

Page 1 of 1

It is certified that error appears in the above-identified patent and that said Letters Patent is hereby corrected as shown below:

In the Specification

Column 18, Line 42, delete "110E" and insert -- 110F -- therefor.

Column 19, Line 10, delete "200E" and insert -- 200F -- therefor.

Column 20, Line 25, delete "400E" and insert -- 400F -- therefor.

Column 21, Line 44, delete "660E" and insert -- 660F -- therefor.

Column 21, Line 49, delete "680E" and insert -- 680F -- therefor.

Signed and Sealed this  
Eighteenth Day of July, 2017

Joseph Matal  
*Performing the Functions and Duties of the*  
*Under Secretary of Commerce for Intellectual Property and*  
*Director of the United States Patent and Trademark Office*